(12) United States Patent
Garti et al.

(10) Patent No.: US 7,390,807 B2
(45) Date of Patent: *Jun. 24, 2008

(54) CRYSTAL FORMS OF LAMOTRIGINE AND PROCESSES FOR THEIR PREPARATIONS

(75) Inventors: Nissim Garti, Ramot (IL); Yana Berkovich, Jerusalem (IL); Ben-Zion Dolitzky, Petach Tiqva (IL); Judith Aronhime, Rehovot (IL); Claude Singer, Kfar Saba (IL); Anita Liebermann, Tel-Aviv (IL); Neomi Gershon, Rosh Ha-Ain (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 95 days.

This patent is subject to a terminal disclaimer.

(21) Appl. No.: 11/045,355

(22) Filed: Jan. 31, 2005

(65) Prior Publication Data

US 2005/0171107 A1 Aug. 4, 2005

Related U.S. Application Data

(63) Continuation of application No. 10/086,157, filed on Feb. 27, 2002, now Pat. No. 6,861,426.

(60) Provisional application No. 60/271,688, filed on Feb. 27, 2001.

(51) Int. Cl.
*A61K 31/53* (2006.01)
*C07D 253/07* (2006.01)

(52) U.S. Cl. .................................. 514/242; 544/182
(58) Field of Classification Search ................ 544/182; 514/242
See application file for complete search history.

(56) References Cited

U.S. PATENT DOCUMENTS

| 4,486,354 | A | | 12/1984 | Baxter et al. |
|---|---|---|---|---|
| 4,560,687 | A | | 12/1985 | Baxter et al. |
| 4,602,017 | A | * | 7/1986 | Sawyer et al. ............. 514/242 |
| 4,847,249 | A | | 7/1989 | Sawyer et al. |
| 5,643,591 | A | | 7/1997 | Mehra et al. |
| 5,861,179 | A | | 1/1999 | Hiskett et al. |
| 5,925,755 | A | | 7/1999 | Lee |
| 5,942,510 | A | | 8/1999 | Floyd et al. |
| 6,124,308 | A | | 9/2000 | Nobbs et al. |
| 6,492,379 | B1 | | 12/2002 | Redkar et al. |
| 6,525,185 | B1 | | 2/2003 | Fan et al. |
| 6,538,134 | B2 | | 3/2003 | Crocker et al. |
| 6,639,072 | B1 | | 10/2003 | Radhakrishnan et al. |
| 6,861,426 | B2 | * | 3/2005 | Garti et al. ............. 514/242 |
| 2004/0247689 | A1 | | 12/2004 | Samburski |

FOREIGN PATENT DOCUMENTS

| ES | 8 604 019 | 6/1986 |
|---|---|---|
| WO | WO 96 17611 | 6/1996 |
| WO | WO 97 00681 | 1/1997 |
| WO | WO 00 35888 | 6/2000 |
| WO | WO 01 22938 | 4/2001 |
| WO | WO 01 49669 | 7/2001 |

OTHER PUBLICATIONS

E. Schmitt et al "Moisture-Dependent Crystallization of Amorphous Lamotrigine Mesylate" Journal of Phamaceutical Sciences vol. 85, No. 11, Nov. 1996, pp. 1215-1219.

Brittain, H.G., Polymorphisim in Pharmaceutical Solids pp. 66, 128-129, 183, 185-186, 203, 205-209, 228-229, 235-236, Marcel Dekker 1999.

Brunauer, S., P.H. Emmett, E. Teller, J. Am. Chem. Soc., 1938, 60, 309-319.

Perry's Chemical Engineers Handbook, 6$^{th}$ ed. p. 15-21 (1984).

* cited by examiner

*Primary Examiner*—Peter O'Sullivan
(74) *Attorney, Agent, or Firm*—Kenyon & Kenyon LLP

(57) ABSTRACT

The present invention relates to lamotrigine, a useful agent for anti-epilepsia. New crystal forms of lamotrigine containing molecules of the solvent in stoichiometric ratios are disclosed. The present invention also provides processes for preparing the new crystal forms of lamotrigine.

13 Claims, 18 Drawing Sheets

CRYSTAL FORMS OF LAMOTRIGINE AND PROCESSES FOR THEIR PREPARATIONS

CROSS-REFERENCE TO RELATED APPLICATION

This application is a continuation of U.S. patent application Ser. No. 10/086,157, now U.S. Pat. No. 6,361,426, filed on Feb. 27, 2002, which claims the benefit under 35 U.S.C. §1.119(e) of Provisional Application Ser. No.60/271,688, filed Feb. 27, 2001. The disclosures of application Ser. Nos. 10/086,157 and 60/271,688 are incorporated by reference in their entireties herein.

FIELD OF THE INVENTION

The present invention relates to new crystal forms of lamotrigine, related pharmaceutical composition, and processes for their preparation.

BACKGROUND OF THE INVENTION

Lamotrigine is known as 6-(2,3-Dichlorophenyl)-1,2,4-triazine-3,5-diamine or 3,5-diamine-6-(2,3-dichlorophenyl)-1,2,4-triazine and has the following chemical formula (I).

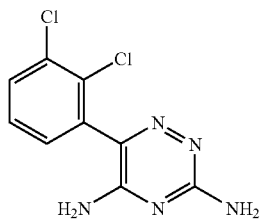

(I)

Lamotrigine is an anti-epileptic drug of the phenyltriazine class and is chemically unrelated to other existing anti-epileptic drugs. This drug is produced by GlaxoWellcome and is sold under the trademark LAMICTAL®. LAMICTAL® is produced in the form of chewable dispersible tablets and is available in different strengths (from 2 mg to 200 mg).

The crystallographic structure of lamotrigine methanolate is known (Acta Cryst., (1989, C45, 129-132)).

No indication was found in the literature concerning the existence of other types of crystal forms of lamotrigine. There is a need to develop various crystal forms of lamotrigine for better formulation.

OBJECTS AND SUMMARY OF THE INVENTION

An object of the present invention is to provide new solvated forms and hydrate forms of lamotrigine.

Another object of the present invention is to provide process for obtaining an anhydrous form A by heating to prepare solvated and hydrate forms of lamotrigine.

The present invention provides a new crystal form B of lamotrigine (a solvate of DMF), characterized by an X-ray powder diffraction pattern having strong peaks at about 10.3, 24.2, 25.0, 26.4, 32.3±0.2 degrees two-theta, and other typical peaks at about 13.0, 15.8, 17.2, 18.5, 20.5, 21.1, 21.7, 26.1, 27.7, 29.5, 30.9±0.2 degrees two-theta.

The present invention provides a new crystal form C of lamotrigine (a solvate of DMF), characterized by an X-ray powder diffraction pattern having a strong peak at about 10.1, 10.5, 17.2, 18.4, 26.6±0.2 degrees two-theta, and other typical peaks at about 12.4, 13.1, 13.6, 14.4, 16.3, 21.6, 22.5, 23.1, 24.4, 27.4, 27.8, 28.4, 32.7, 33.6, 34.6±0.2 degrees two-theta.

The present invention provides a new crystal form D of lamotrigine (a solvate of DMF), characterized by an X-ray powder diffraction pattern having a strong peak at about 14.1, 15.9, 18.2, 20.6, 30.8±0.2 degrees two-theta and other typical peaks at about 13.2, 14.9, 17.2, 18.0, 19.0, 19.5, 22.7, 23.0, 23.5, 26.2, 27.0, 27.8, 28.2, 28.6, 29.0, 29.5, 31.0, 32.9, 33.8±0.2 degrees two-theta.

The present invention provides a new crystal form E of lamotrigine (a methanolate), characterized by an X-ray powder diffraction pattern having a strong peak at about 9.5, 11.5, 13.8, 23.2, 26.7±0.2 degrees two-theta and other typical peaks at about 13.0, 14.3, 14.9, 15.7, 17.9, 19.4, 20.9, 24.5, 25.6, 27.3, 32.2±0.2 degrees two-theta.

The present invention provides a new crystal form E1 of lamotrigine (an ethanolate), characterized by an X-ray powder diffraction pattern having a strong peak at about 9.6, 13.8, 15.8, 23.1, 26.7±0.2 degrees two-theta and other typical peaks at about 11.6, 13.0, 14.4, 15.2, 16.2, 17.8, 18.9, 20.1, 21.8, 24.6, 25.6, 26.3, 27.3, 27.7, 28.8, 30.0, 30.7, 31.9, 32.3, 32.7, 34.3, 35.9±0.2 degrees two-theta.

The present invention provides a new crystal form F of lamotrigine (an acetonate), characterized by an X-ray powder diffraction pattern having a strong peak at about 17.2, 18.7, 26.5, 27.0, 28.0±0.2 degrees two-theta and other typical peaks at about 9.7, 11.8, 12.7, 13.4, 14.6, 15.4, 20.2, 20.7, 21.3, 21.6, 22.0, 24.6, 25.1, 25.5, 28.2, 29.4, 30.1, 31.8±0.2 degrees two-theta.

The present invention provides a new crystal form H of lamotrigine (an ethanolate), characterized by an X-ray powder diffraction pattern having strong peaks at about 9.6, 10.5, 21.8, 22.2, 27.5±0.2 degrees two-theta and other peaks at about 12.2, 13.5, 14.7, 15.1, 16.5, 16.7, 17.0, 18.5, 19.5, 20.5, 24.0, 24.6, 25.7, 26.3, 28.4, 28.9, 29.4, 30.5, 31.1, 31.8, 33.3, 35.1±0.2 degrees two-theta.

The present invention provides a new crystal form J of lamotrigine (an isopropanolate), characterized by an X-ray powder diffraction pattern having strong peaks at about 9.5, 10.0, 20.2, 26.0±0.2 degrees two-theta and other peaks at about 11.6 12.4, 13.7, 14.8, 15.9, 16.3, 16.6, 17.3, 18.0, 18.5, 20.4, 21.0, 21.3, 24.2, 24.4, 24.7, 25.0, 25.5, 26.4, 26.7, 27.6, 27.8, 28.3, 28.7, 29.2, 30.4, 30.6, 35.1±0.2 degrees two-theta.

The present invention provides a new crystal form K of lamotrigine (a solvate of THF), characterized by an X-ray powder diffraction pattern having strong peaks at about 11.2, 12.9, 17.2, 21.5, 22.3±0.2 degrees two-theta and other peaks at about 13.5, 17.8, 18.4, 19.2, 20.4, 24.3, 25.3, 25.9, 26.7, 27.0, 28.0, 28.4, 29.0, 29.6, 30.2, 30.6, 31.4, 32.4, 34.7±0.2 degrees two-theta.

The present invention provides a new crystal form L of lamotrigine (a solvate of acetonate), characterized by an X-ray powder diffraction pattern having strong peaks at about 12.9, 14.9, 18.2, 20.5, 25.8±0.2 degrees two-theta, and other typical peaks at about 8.3, 11.3, 11.7, 12.4, 14.1, 16.7, 17.6, 18.4, 19.0, 20.1, 21.7, 22.6, 23.6, 24.6, 26.3, 26.8, 27.8, 28.4, 28.9, 31.1, 31.9, 33.3±0.2 degrees two-theta.

The present invention provides a crystal form M of lamotrigine (a solvate of DMA), characterized by an X-ray powder diffraction pattern having strong peaks at about 10.0, 16.5, 16.8, 25.5, 27.4±0.2 degrees two-theta, and other typical peaks at about 9.0, 11.4, 13.0, 13.8, 15.1, 17.4, 17.8, 18.6, 21.1, 21.9, 23.8, 26.5, 27.0, 28.0, 28.6, 29.0, 30.1, 32.1, 33.1, 33.6±0.2 degrees two-theta.

The present invention provides a crystal form N of lamotrigine (hydrate), characterized by an X-ray powder diffraction pattern having strong peaks at about 11.6, 13.4, 15.0, 26.9, 27.7±0.2 degrees two-theta, and other typical peaks at about 15.9, 16.5, 19.1, 22.2, 22.4, 23.2, 23.5, 26.7, 28.6, 29.9, 30.1, 30.4, 30.7, 31.4, 31.9, 32.9, 33.3, 34.4, 35.0, 36.2±0.2 degrees two-theta.

The present invention provides a new crystal form O of lamotrigine (a solvate of methanolate), characterized by an X-ray powder diffraction pattern having strong peaks at about 9.5, 13.7, 23.0, 26.7, 28.7±0.2 degrees two-theta, and other typical peaks at about 8.5, 11.4, 14.2, 15.7, 18.0, 18.9, 24.2, 25.6, 25.9, 27.7, 30.0, 30.7, 32.6, 34.3, 34.8±0.2 degrees two-theta.

The present invention provides a crystal form P of lamotrigine (a solvate of DMF), characterized by an X-ray powder diffraction pattern having strong peaks at about 16.1, 18.1, 18.7, 26.0±0.2 degrees two-theta, and other typical peaks at 8.4, 9.0, 10.1, 12.1, 13.3, 19.5, 20.4, 21.8, 22.5, 24.0, 24.4, 27.4, 28.3±0.2 degrees two-theta.

The present invention provides a crystal form Q of lamotrigine (a monosolvate of isopropanolate), characterized by an X-ray powder diffraction pattern having strong peaks at about 12.4, 13.8, 14.1, 16.6, 17.4, 17.9, 20.0, 21.0, 23.6, 28.8, 30.9±0.2 degrees two-theta, and other typical peaks at about 9.4, 10.0, 26.7, 27.8, and 28.4±0.2 degrees two-theta.

The present invention provides a crystal form R of lamotrigine (a monosolvate of methyl-isobutyl-ketone), characterized by an X-ray powder diffraction pattern having strong peaks at about 10.9, 12.2, 21.0, 27.3, 28.6, 32.5±0.2 degrees and other typical peaks at about 8.2, 15.7, 19.0, 23.5 and 25.4±0.2 degrees two-theta.

The present invention provides a crystal form S of lamotrigine (anhydrous), characterized by an X-ray powder diffraction pattern having strong peaks at about 13.4, and 18.7±0.2 degrees two-theta and other typical peaks at about 22.4, 26.0, 27.6, and 31.3±0.2 degrees two-theta.

The present invention provides a crystal form U of lamotrigine (a monosolvate of MTBE), characterized by an X-ray powder diffraction pattern having strong peaks at about 12.4, 19.5, 28.4, 32.1±0.2 degrees two-theta and other typical peaks at about 11.5, 15.9, 17.9, 25.4, 25.8, and 26.6±0.2 degrees two-theta.

The present invention provides a method of making lamotrigine forms B, C, D, E, E1, and F by solvent/anti-solvent crystallization.

The present invention provides a method of making lamotrigine forms H, O, and J by crystallization in solution.

The present invention provides a method of making lamotrigine forms C, H, J, K, L, M, and N by treating lamotrigine anhydrous in solvents.

The present invention provides a method of making lamotrigine form P by heating form C at about 80° C. to about 110° C. for about 1 hour.

The present invention provides a method of preparing a lamotrigine form B, comprising the steps of 1) dissolving lamotrigine anhydrous in DMF at about 70° C.; 2) precipitating the lamotrigine form B by adding water at about 0° C.; and 3) filtering the lamotrigine form B.

The present invention provides a method of preparing a lamotrigine form C, comprising the steps of 1) dissolving lamotrigine anhydrous in DMF at about 70° C.; 2) precipitating the lamotrigine form C by adding chloroform at about 0° C.; and 3) filtering the lamotrigine form C.

The present invention provides a method of preparing a lamotrigine form C, comprising the steps of 1) dissolving lamotrigine anhydrous in DMF at about 70° C.; 2) precipitating the lamotrigine form C by adding toluene at about 0° C.; and 3) filtering the lamotrigine form C.

The present invention provides a method of preparing a lamotrigine form C, comprising the steps of 1) dissolving lamotrigine anhydrous in DMF at about 70° C.; 2) precipitating the lamotrigine form C by adding acetone at about 0° C.; and 3) filtering the lamotrigine form C.

The present invention provides a method of preparing lamotrigine form C, comprising the steps of 1) dissolving lamotrigine anhydrous in DMF to form a solution; 2) stirring the solution at about 25° C. for about 24 hours; and 3) filtering the lamotrigine form C.

The present invention provides a method of preparing a lamotrigine form D, comprising the steps of 1) dissolving lamotrigine anhydrous in DMF at about 70° C.; 2) precipitating the lamotrigine form D by adding water; and 3) filtering the lamotrigine form D.

The present invention provides a method of preparing a lamotrigine form E, comprising the steps of 1) dissolving lamotrigine anhydrous in methanol at about 55° C.; 2) precipitating the lamotrigine form E by adding toluene at about 0° C.; and 3) filtering the lamotrigine form E.

The present invention provides a method of preparing a lamotrigine form E1, comprising the steps of 1) dissolving lamotrigine anhydrous in ethanol at about 0° C.; 2) precipitating the lamotrigine form E1 by adding toluene at about 55° C., and 3) precipitating the lamotrigine form E1.

The present invention provides a method of preparing lamotrigine form F, comprising the steps of 1) dissolving lamotrigine anhydrous in acetone at about 70° C.; 2) precipitating the lamotrigine form F by adding cyclohexane at about 0° C.; and 3) precipitating the lamotrigine by adding cyclohexane.

The present invention provides a method of preparing lamotrigine form H, comprising the steps of 1) dissolving lamotrigine anhydrous in ethanol to form a solution; 2) stirring the solution at about 25° C. for about 24 hours; and 3) filtering the lamotrigine form H.

The present invention provides a method of preparing lamotrigine form H, comprising the steps of 1) dissolving lamotrigine anhydrous in isopropanol to form a solution; 2) heating the solution at about 65° C.; 3) cooling the solution to about 25° C. for about 5.5 hours; 4) filtering the solution; and 5) drying the solution at about 50° C. for about 17 hours at about 10 mmHg.

The present invention provides a method of preparing Lamotrigine form J, comprising the steps of 1) dissolving lamotrigine anhydrous in isopropanol to form a solution; 2) heating the solution to about 65° C.; 3) cooling the solution to about 25° C. for about 5.5 hours; 4) filtering the solution; and 5) drying the solution at about 50° C. for about 17 hours at about 10 mmHg.

The present invention provides a method of preparing lamotrigine form K, comprising the steps of 1) dissolving lamotrigine anhydrous in THF to form a solution; 2) stirring the solution at about 25° C. for about 24 hours; and 3) filtering the lamotrigine form K.

The present invention provides a method of preparing lamotrigine form L, comprising the steps of 1) dissolving lamotrigine anhydrous in acetone to form a solution; 2) stirring the solution at about 25° C. for about 24 hours; 3) concentrating the solution to dryness; 4) adding acetone; and 5) filtering the lamotrigine form L.

The present invention provides a method of preparing lamotrigine form M, comprising the steps of 1) dissolving lamotrigine anhydrous in DMA to form a solution; 2) stirring the solution at about 25° C. for about 24 hours; and 3) filtering the lamotrigine form M.

The present invention provides a method of preparing lamotrigine form N, comprising the steps of 1) dissolving lamotrigine anhydrous in water to form a solution; 2) stirring the solution at about 25° C. for about 24 hours; and 3) filtering the lamotrigine form N.

The present invention provides a method of preparing lamotrigine form O, comprising the steps of 1) dissolving lamotrigine anhydrous in methanol to form a solution; 2) heating the solution to about 65° C.; 3) cooling the solution to about 25° C. for about 5.5 hours; 4) filtering the solution; and 5) drying the solution at 60° C. for about 17 hours at about 10 mmHg.

The present invention provides a method of preparing lamotrigine form P, wherein the lamotrigine from P is prepared by heating lamotrigine form C monosolvate at about 80° C. for about 1 hour.

The present invention provides a method of preparing lamotrigine amorphous, wherein the lamotrigine amorphous is produced by heating lamotrigine form J isopropanolate at about 80° C. for about 1 hour.

The present invention provides a method of preparing lamotrigine form Q, comprising the steps of 1) dissolving lamotrigine anhydrous in isopropanol to form a solution; 2) heating the solution at about 65° C. for about 5 minutes; 3) cooling the solution to room temperature; and 3) filtering the lamotrigine form Q.

The present invention provides a method of preparing lamotrigine form R, comprising the steps of 1) dissolving lamotrigine anhydrous in methyl-isobutyl-ketone (MIBK) to form a solution; 2) heating the solution at about 65° C. for about 5 minutes; 3) cooling the solution to room temperature; 4) stirring the solution; and 5) filtering the lamotrigine form R.

The present invention provides a method of preparing lamotrigine form S, comprising the steps of 1) dissolving lamotrigine anhydrous in DMC to form a solution; 2) heating the solution at about 65° C. for about 5 minutes; 3) cooling the solution to room temperature; 4) stirring the solution; and 5) filtering the lamotrigine form S.

The present invention provides a method of preparing lamotrigine form U, comprising the steps of 1) dissolving lamotrigine anhydrous in MTBE to form a solution; 2) heating the solution at about 65° C. for about 5 minutes; 3) cooling the solution to room temperature; 4) stirring the solution; and 5) filtering the lamotrigine form U.

DETAILED DESCRIPTION OF THE INVENTION

Figure 1:
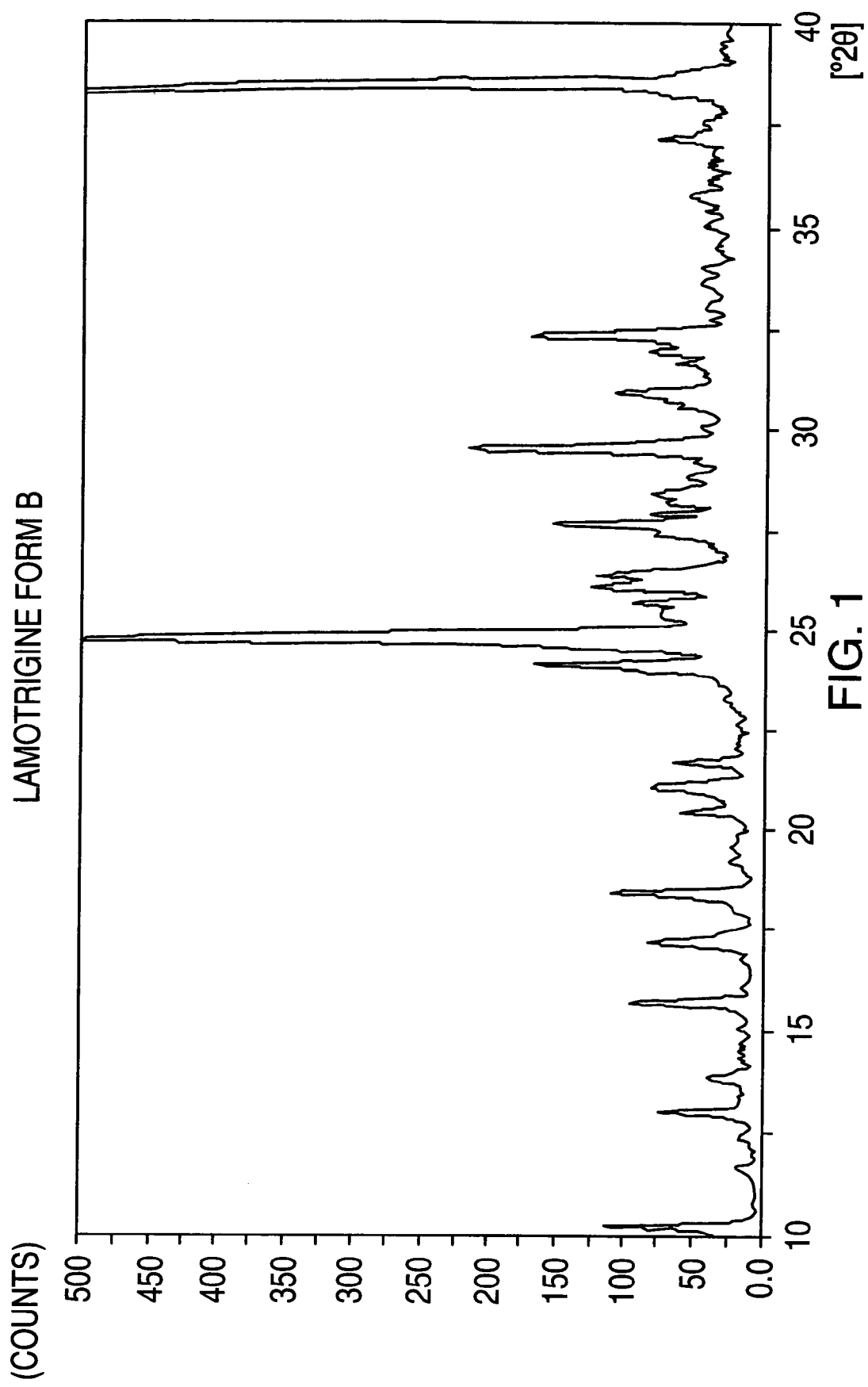
FIG. 1 shows the X-ray diffraction pattern of lamotrigine form B.
Figure 2:
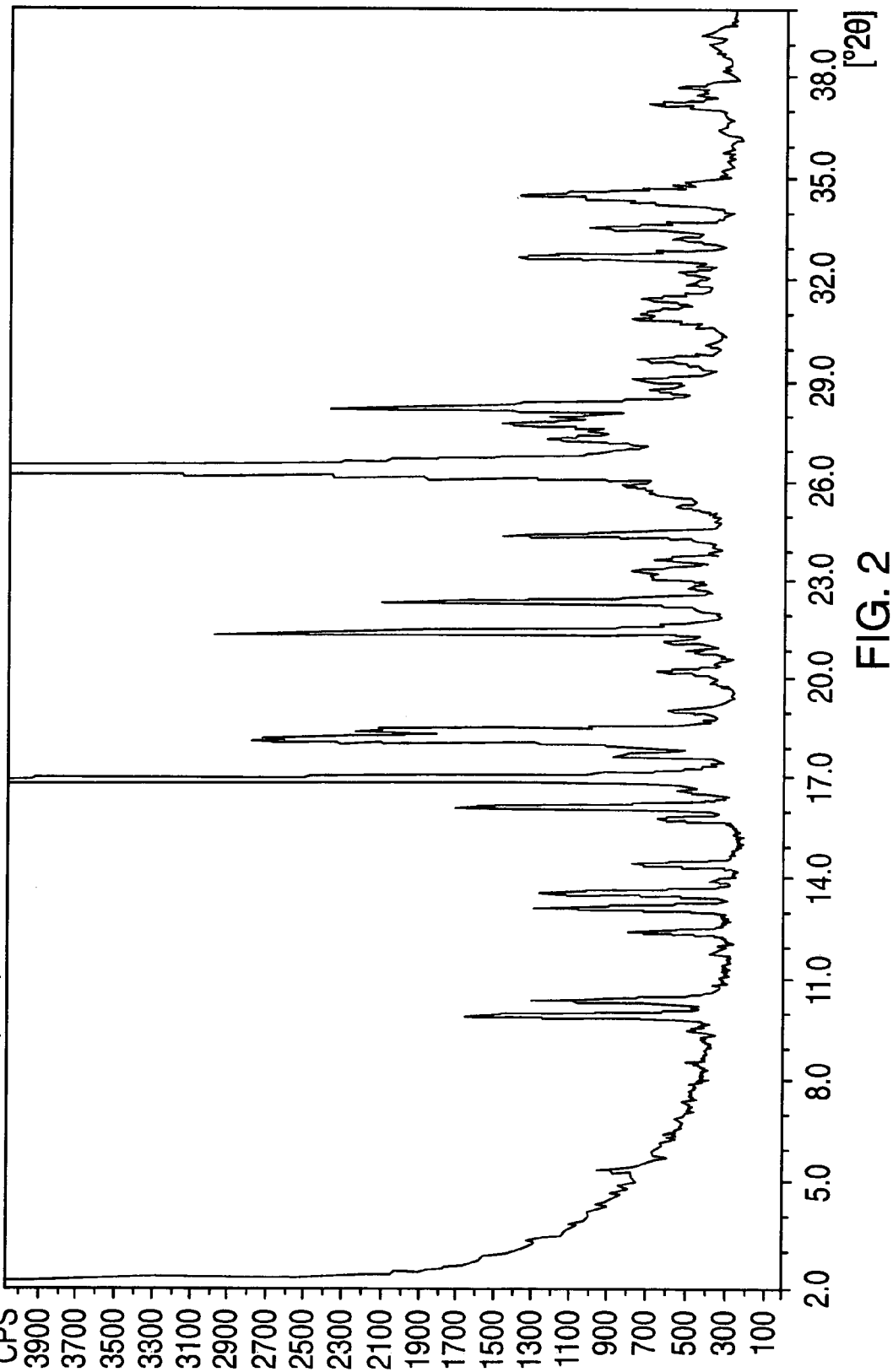
FIG. 2 shows the X-ray diffraction pattern of lamotrigine form C.
Figure 3:
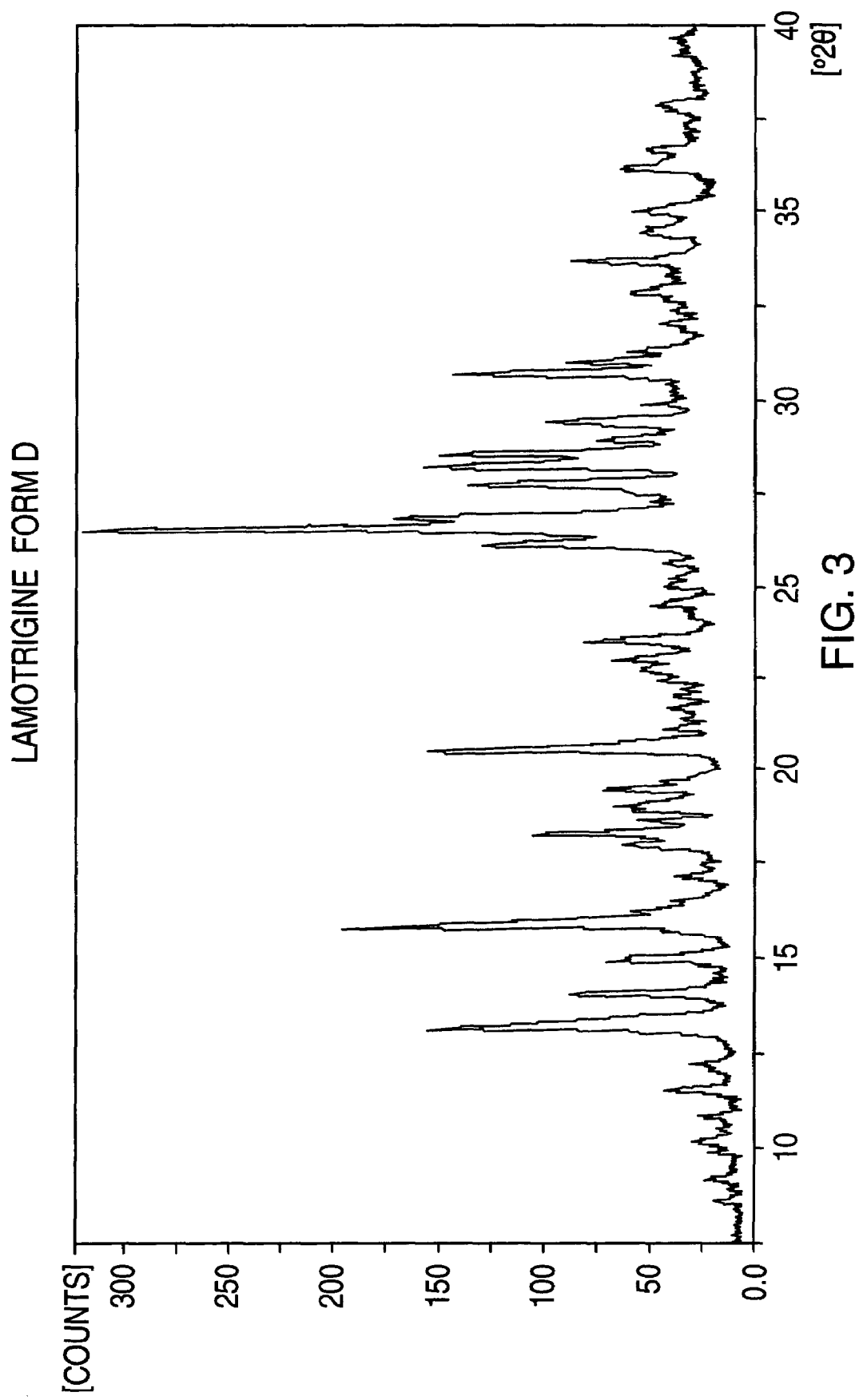
FIG. 3 shows the X-ray diffraction pattern of lamotrigine form D.

Definitions:

As used herein, the term "TGA" refers to thermogravimetric analysis. The Karl Fisher assay for determining water content is used which is described in *Pharmacopeial Form*, Vol. 24, No. 1, p. 5438 (January-February 1998). Such an assay permits the determination of water content of a crystal form based on the Loss on Drying Method. TGA is a measure of the thermally induced weight loss of a material as a function of the applied temperature. TGA is restricted to transitions that involve either a gain or a loss of mass, and it is most commonly used to study desolvation processes and compound decomposition. One skilled in the art will appreciate that other commonly thermal analyses can also be used, such as differential scanning calorimetry.

As used herein, the term "DMF" refers to dimethylformamide; the term ATHF@ refers to tetrahydrofuran; the term "MIBK" refers to methyl-isobutyl-ketone; the term "DMC" refers to dimethylcarbinol; the term "MTBE" refers to methyl tertiary-butyl ether; the term "IPA" refers to isopropyl alcohol; the term "THF" refers to tetrahydrofuran; and the term "DMA" refers to dimethylamine. One skilled in the art will appreciate the term "anti-solvent" refer to a solvent, when added to a solution of a lamotrigine, causes the precipitation of lamotrigine. Exemplary anti-solvents include acetone, toluene, cyclohexane, water and the like.

As used herein, the term "anhydrous" when used in reference to lamotrigine refers to a lamotrigine crystal form that is substantially free of water.

As used herein, the terms "methanolate", "ethanolate" and "isopropanolate" refer to lamotrigine in which the respective solvent is contained within the crystal lattice of lamotrigine in a quantity above 1%.

As used herein, the term "monosolvate of DMF" when used in reference to lamotrigine describes a crystal form of lamotrigine having a TGA weight loss up to about 20%.

As used herein, the term "sesquisolvate of DMF" when used in reference to lamotrigine describes a crystal form of lamotrigine having a TGA weight loss up to about 30%.

As used herein, the term "⅔ solvate of DMF" when used in reference to lamotrigine describes a crystal form of lamotrigine having a TGA weight loss up to about 16%.

As used herein, the term "⅔ methanolate" when used in reference to lamotrigine describes a crystal form of lamotrigine having a TGA weight loss up to about 8%.

As used herein, the term "⅓ solvate of acetone" when used in reference to lamotrigine describes a crystal form of lamotrigine having a TGA weight loss up to about 6.3%.

As used herein, the term "monosolvate of ethanol" when used in reference to lamotrigine describes a crystal form of lamotrigine having a TGA weight loss up to about 15%.

As used herein, the term "monosolvate of methanol" when used in reference to lamotrigine describes a crystal form of lamotrigine having a TGA weight loss up to about 11%.

As used herein, the term "monosolvate of isopropanol" when used in reference to lamotrigine describes a crystal form of lamotrigine having a TGA weight loss up to about 19%.

As used herein, the term "solvate of THF" when used in reference to lamotrigine describes a crystal form of lamotrigine having a TGA weight loss up to about 23%.

As used herein, the term "solvate of acetone" when used in reference to lamotrigine describes a crystal form of lamotrigine having a TGA weight loss up to about 19%.

As used herein, the term "solvate of DMF" when used in reference to lamotrigine describes a crystal form of lamotrigine having a TGA weight loss up to about 20%.

As used herein, the term "hydrate" when used in reference to lamotrigine describes a crystal form of lamotrigine having a water content up to about 6.6%.

As used herein, the term "2/3 methanolate" when used in reference to lamotrigine describes a crystal form of lamotrigine having a TGA weight loss up to about 7.2%.

Solid-state chemistry of a crystal cannot predicate whether an organic solvent can incorporate into the crystal. The manner in which solvation of a crystal may occur is also unpredictable. There are no rules exist that allow prediction of whether a compound will exist as solvated forms of an organic solvent.

The discovery of new solvated forms of a pharmaceutically useful compound may provide an opportunity to improve the performance characteristics of a pharmaceutical product. It enlarges the repertoire of materials that a formulation scientist has available for designing, for example, a pharmaceutical dosage form of a drug with a targeted release profile or other desired characteristic. It is clearly advantageous when this repertoire is enlarged by the discovery of new solvated crystalline forms of a useful compound.

The present invention relates to the solvated crystal forms of lamotrigine. Different crystal forms of lamotrigine may possess different physical properties include, for example, the flowability of the milled solid. Flowability affects the ease with which the material is handled during processing into lamotrigine. When particles of the powdered compound do not flow past each other easily, a formulation specialist must take that fact into account in developing a tablet or capsule formulation, which may necessitate the use of glidants such as colloidal silicon dioxide, talc, starch or tribasic calcium phosphate.

Another important physical property of solvated/hydrated crystal forms of lamotrigine relate to its rate of dissolution in aqueous fluid. The rate of dissolution of an active ingredient in a patient's stomach fluid can have therapeutic consequences since it imposes an upper limit on the rate at which an orally-administered active ingredient can reach the patient's bloodstream. The rate of dissolution is also a consideration in formulating syrups, elixirs and other liquid medicaments. The solid state form of a compound may also affect its behavior on compaction and its storage stability.

All X-ray powder diffraction patterns were obtained by methods known in the art. One method employs the use of a Philips X-Ray powder diffractometer, Goniometer model 1050/70 at a scanning speed of 2° per minute. Another method employs the use of a Scintag X'TRA X-ray powder diffractometer, equipped with a solid state Si(Li) detector thermoelectrically cooled, at a scanning speed of 3° min.$^{-1}$ Scanning range 2-40 degrees two-theta. Copper radiation of =1.5418 Å was used.

The properties of solvated crystal forms of lamotrigine may differ from that of LAMICTAL; they include solubility, stability, hygroscopicity (ability to remove moisture from air), tabletability, bioavailability, storage life (shelf life), and flow properties.

Preparation of Anhydrous Form A by Heating

According to one embodiment, the present invention provides a process for preparing lamotrigine form A including heating lamotrigine solvates at temperatures elevated enough to remove all the solvent from the crystal, usually above 100° C. for a period of about 2 hours, preferably above 110° C. for a period of about 1 hour, more preferably at about 150° C. for a period of about 2 hour.

Novel Crystal Forms of Lamotrigine Solvates Form P-Monosolvate of DMF

According to one embodiment, the present invention provides a novel crystal form of lamotrigine denominated form P, which is a monosolvate of DMF. lamotrigine form P exhibits strong X-ray powder diffraction peaks at about 16.1, 18.1, 18.7, 26.0±0.2 degrees two-theta, and other typical peaks at about 8.4, 9.0, 10.1, 12.1, 13.3, 19.5, 20.4, 21.8, 22.5, 24.0, 24.4, 27.4, 28.3±0.2 degrees two-theta.

This sample shows a TGA weight loss of about 20%, which is a monosolvate of DMF.

According to another embodiment, the present invention provides a process for preparing lamotrigine form P including heating lamotrigine form C monosolvate of DMF at a temperature below the temperature of desolvation, about 60° C. for a period of about 3 hours, preferably at about 80° C. for a period of about 1 hour.

Amorphous Lamotrigine

According to one embodiment, the present invention provides a novel amorphous form of lamotrigine.

According to another embodiment, the present invention provides a process for preparing lamotrigine amorphous including heating lamotrigine J isopropanolate at about 80° C. for about 1 hour.

Novel Solvated Crystal Forms Obtained by Crystallization Using Solvent/Anti-Solvent Technique, and Processes Form B-monosolvate of DMF According to one embodiment, the present invention provides a novel crystal form of lamotrigine denominated form B, which is a monosolvate of DMF. lamotrigine form B exhibits strong X-ray diffraction peaks at about 10.3, 24.2, 25.0, 26.4 and 32.3±0.2 degrees two-theta, and other typical peaks at about 13.0, 15.8, 17.2, 18.5, 20.5, 21.1, 21.7, 26.1, 27.7, 29.5, 30.9±0.2 degrees two-theta.

This sample shows a TGA weight loss up to about 120° C. of about 20%, which corresponds to the monosolvate of DMF.

According to another aspect, the present invention relates to a process including dissolution at high concentration in DMF and precipitation by addition of an anti-solvent like water.

Form C-Sesquisolvate of DMF

According to one embodiment, the present invention provides a novel crystal form of lamotrigine denominated form C, which is a sesquisolvate of DMF. lamotrigine form C exhibits strong X-ray diffraction peaks at about 10.1, 10.5, 17.1, 18.4, 26.6±0.2 degrees two-theta, and other typical peaks at about 12.4, 13.1, 13.6, 14.4, 16.3, 21.6, 22.5, 23.1, 24.4, 27.4, 27.8, 28.4, 32.7, 33.6, 34.6±0.2 degrees two-theta.

This sample shows a TGA weight loss of about 30%, which corresponds to the sesquisolvate of DMF.

According to another embodiment, the present invention provides a process for preparing lamotrigine form C including dissolving lamotrigine in DMF, and precipitating by addition of chloroform, or acetone, or toluene.

Form D-⅔ Solvate of DMF

According to one embodiment, the present invention provides a novel crystal form of lamotrigine denominated form D, which is a ⅔ solvate of DMF. Lamotrigine form D exhibits strong X-ray diffraction peaks at about 14.1, 15.9, 18.2, 20.6, 30.8±0.2 degrees two-theta and other typical peaks at about 13.2, 14.9, 17.2, 18.0, 19.0, 19.5, 22.7, 23.0, 23.5, 26.2, 27.0, 27.8, 28.2, 28.6, 29.0, 29.5, 31.0, 32.9, 33.8±0.2 degrees two-theta.

This sample shows a TGA weight loss of about 16%, which corresponds to the ⅔ solvate value of DMF.

According to another aspect, the present invention relates to a process including dissolution at low concentration in DMF and precipitation by addition of an anti-solvent like water.

Form E-⅔ Methanolate

According to one embodiment, the present invention provides a novel crystal form of lamotrigine denominated form E, which is a ⅔ solvate of methanol. Lamotrigine form E exhibits strong X-ray diffraction peaks at about 9.5, 11.5, 13.8, 23.2, 26.7±0.2 degrees two-theta and other typical peaks at about 13.0, 14.3, 14.9, 15.7, 17.9, 19.4, 20.9, 24.5, 25.6, 27.3, 32.2±0.2 degrees two-theta.

This sample shows a TGA weight loss of about 8%, which corresponds to the 2/3 solvate value of methanol.

According to another aspect, the present invention relates to a process including dissolution in methanol and precipitation by addition of toluene.

Form E1-⅔ Ethanolate

According to one embodiment, the present invention provides a novel crystal form of lamotrigine denominated form E, which is a ⅔ solvate of ethanol. Lamotrigine form E1 exhibits strong X-ray diffraction peaks at about 9.6, 13.8, 15.8, 23.1, 26.7±0.2 degrees two-theta and other typical peaks at about 11.6, 13.0, 14.4, 15.2, 16.2, 17.8, 18.9, 20.1, 21.8, 24.6, 25.6, 26.3, 27.3, 27.7, 28.8, 30.0, 30.7, 31.9, 32.3, 32.7, 34.3, 35.9±0.2 degrees two-theta.

This sample shows a TGA weight loss of about 9.5%, which corresponds to the ⅔ solvate value of ethanol.

According to another embodiment, the present invention provides a process of preparing lamotrigine form E1 including dissolution in ethanol and precipitation by addition of an anti-solvent like toluene.

Form F-⅓ Solvate of Acetone

According to one embodiment, the present invention provides a novel crystal form of lamotrigine denominated form F, which is a ⅓ solvate of acetone. Lamotrigine form F exhibits strong X-ray powder diffraction peaks at about 17.2, 18.7, 26.5, 27.0, 28.0±0.2 degrees two-theta and other typical peaks at about 9.7, 11.8, 12.7, 13.4, 14.6, 15.4, 20.2, 20.7, 21.3, 21.6, 22.0, 24.6, 25.1, 25.5, 28.2, 29.4, 30.1, 31.8±0.2 degrees two-theta.

This sample shows a TGA weight loss of about 6.3%, which corresponds to the ⅓ of acetone.

According to another embodiment, the present invention provides a process including dissolution in acetone and precipitation by addition of an anti-solvent like cyclohexane.

Novel Solvated/Hydrates Forms Obtained by Slurry of Lamotrigine, and Processes Form C-Monosolvate of DMF According to one embodiment, the present invention provides a process for preparing lamotrigine form C monosolvate of DMF including treating lamotrigine anhydrous in DMF.

This sample shows a TGA weight loss of about 21%, which corresponds to the monosolvate of DMF.

According to another embodiment, the present invention provides a process for preparing lamotrigine form C by treating lamotrigine in DMF for the duration of one day.

Form H-Monosolvate of Ethanol

According to one embodiment, the present invention provides a novel crystal form of lamotrigine denominated form H, which is a monosolvate of ethanol. Lamotrigine form H has strong X-ray diffraction peaks at about 9.6, 10.5, 21.8, 22.2, 27.5±0.2 degrees two-theta and other peaks at about 12.2, 13.5, 14.7, 15.1, 16.5, 16.7, 17.0, 18.5, 19.5, 20.5, 24.0, 24.6, 25.7, 26.3, 28.4, 28.9, 29.4, 30.5, 31.1, 31.8, 33.3, 35.1±0.2 degrees two-theta.

This sample shows a TGA weight loss of about 15%, which corresponds to the monoethanolate.

According to another embodiment, the present invention provides a process including treating lamotrigine in ethanol for the duration of 1 day.

According to another aspect, the present invention relates to a process including treating lamotrigine in methanol for the duration of 1 day.

Form J-Monosolvate of Isopropanol

According to one embodiment, the present invention provides a novel crystal form of lamotrigine denominated form J, which is a monoisopropanolate. Lamotrigine form J has strong X-ray powder diffraction peaks at about 9.5, 10.0, 20.2, 26.0,±0.2 degrees two-theta and otherpeaks at about 11.6, 12.4, 13.7, 14.8, 15.9, 16.3, 16.6, 17.3, 18.0, 18.5, 20.4, 21.0, 21.3, 24.2, 24.4, 24.7, 25.0, 25.5, 26.4, 26.7, 27.6, 27.8, 28.3.28.7, 29.2, 30.4, 30.6, 35.1±0.2 degrees two-theta.

This sample shows a TGA weight loss of about 19%, which corresponds to the monoisopropanolate.

According to another aspect, the present invention provides a process of making lamotrigine form J including treating lamotrigine form A in isopropanol for the duration of 1 day.

Form K-Solvate of THF

According to one embodiment, the present invention provides a novel crystal form of lamotrigine denominated form K, which is a solvate of THF. Lamotrigine form K has strong X-ray powder diffraction peaks at about 11.2, 12.9, 17.2, 21.5, 22.3±0.2 degrees two-theta and other peaks at about 13.5, 17.8, 18.4, 19.2, 20.4, 24.3, 25.3, 25.9, 26.7, 27.0, 28.0, 28.4, 29.0, 29.6, 30.2, 30.6, 31.4, 32.4, 34.7±0.2 degrees two-theta.

This sample shows a TGA weight loss of about 23%, which corresponds to the monosolvate of THF.

According to another embodiment, the present invention provides a process of making lamotrigine form K including treating lamotrigine in THF for the duration of 1 day.

Form L-Solvate of Acetone

According to one embodiment, the present invention provides a novel crystal form of lamotrigine denominated form L, which is a monosolvate of acetone. Lamotrigine form L exhibits strong X-ray powder diffraction peaks at about 12.9, 14.9, 18.2, 20.5, 25.8±0.2 degrees two-theta, and other typical peaks at about 8.3, 11.3, 11.7, 12.4, 14.1, 16.7, 17.6, 18.4, 19.0, 20.1, 21.7, 22.6, 23.6, 24.6, 26.3, 26.8, 27.8, 28.4, 28.9, 31.1, 31.9, 33.3±0.2 degrees two-theta.

This sample shows a TGA weight loss of about 19%, which is a monosolvate of acetone.

According to another embodiment, the present invention provides a process of making lamotrigine form L including treating lamotrigine in acetone for the duration of one day.

Form M-Solvate of DMA

According to one embodiment, the present invention provides a novel crystal form of lamotrigine denominated form M, which is a monosolvate of DMA. Lamotrigine form M exhibits strong X-ray powder diffraction peaks at about 10.0, 16.5, 16.8, 25.5, 27.4±0.2 degrees two-theta, and other typical peaks at about 9.0, 11.4, 13.0, 13.8, 15.1, 17.4, 17.8, 18.6, 21.1, 21.9, 23.8, 26.5, 27.0, 28.0, 28.6, 29.0, 30.1, 32.1, 33.1, 33.6 degrees two-theta.

This sample shows a TGA weight loss of about 20%, which is a monosolvate of DMA.

According to another embodiment, the present invention provides a process of making lamotrigine form M including treating lamotrigine in DMA for the duration of one day.

Form N-Hydrate

According to one embodiment, the present invention provides a novel crystal form of lamotrigine denominated form N, which is a monohydrate. Lamotrigine form N exhibits strong X-ray powder diffraction peaks at about 11.6, 13.4, 15.0, 26.9, 27.7±0.2 degrees two-theta, and other typical peaks at about 15.9, 16.5, 19.1, 22.2, 22.4, 23.2, 23.5, 26.7, 28.6, 29.9, 30.1, 30.4, 30.7, 31.4, 31.9, 32.9, 33.3, 34.4, 35.0, 36.2 degrees two-theta.

This sample shows a TGA weight loss of about 6.6%, which is a monohydrate.

According to another embodiment, the present invention provides a process of lamotrigine form N including treating lamotrigine in water for the duration of one day.

Novel Crystal Form Obtained by Crystallization of Solution Form O-⅔ Methanolate

According to one embodiment, the present invention provides a novel crystal form of lamotrigine denominated form O, which is ⅔ methanolate. Lamotrigine form O exhibits strong X-ray powder diffraction peaks at about 9.5, 13.7, 23.0, 26.7, 28.7±0.2 degrees two-theta, and other typical peaks at about 8.5, 11.4, 14.2, 15.7, 18.0, 18.9, 24.2, 25.6, 25.9, 27.7, 30.0, 30.7, 32.6, 34.3, 34.8±0.2 degrees two-theta.

This sample shows a TGA weight loss of about 7.2%, which is a ⅔ solvate of methanol.

According to another embodiment, the present invention provides to a process for preparing lamotrigine form O including dissolving in methanol, and crystallizing.

The following table summarizes all the crystal forms of lamotrigine so far obtained.

| Process | Solvent | Crystal form obtained | Weight loss | Solvate, Determined weight loss (TGA) | Expected weight loss |
|---|---|---|---|---|---|
| Crystallization from solvent/anti-solvent | | | | | |
| 1 | DMF/water | B | 20% | Monosolvate of DMF | 22% |
| 2 | DMF/ClCl₃, acetone, toluene | C | 30% | 1.5 solvate of DMF | 30% |
| 3 | DMF/water | D | 16% | ⅔ solvate of DMF | 16% |
| 4 | MeOH/toluene | E | 8% | ⅔ Methanolate | 7.4% |
| 5 | EtOH/toluene | E1 | 9.5% | ⅔ Ethanolate | 10.7% |
| 6 | Acetone/Cyclohexane | F | 6.3% | ⅓ Acetonate | 7.0% |
| Slurry of Lamotrigine Anhydrous | | | | | |
| 7 | DMF | C | 21.6% | Monosolvate of DMF | 22% |
| 8 | Ethanol | H | 15% | Monoethanolate | 15% |
| 9 | Methanol | E1 | 11% | Monomethanolate | 11% |
| 10 | Isopropanol | J | 19% | Monoisopropanolate | 19% |
| 11 | THF | K | 23% | Monosolvate of THF | 22% |
| 12 | Acetone | L | 19% | Monoacetonate | 18% |
| 13 | DMA | M | 20% | Monosolvate of DMA | 15% |
| 14 | Water | N | 6.6% | Monohydrate | 6.6% |
| Crystallization from Solutions | | | | | |
| 15 | EtOH | H | 14.1% | Monoethanolate | 15% |
| 16 | MeOH | O | 7.2% | ⅔ Methanolate | 7.4% |
| 17 | Isopropanol | J | | | |

| Initial Crystal Form | Process | Crystal Form after annealing at 80EC 60 min | Process | Crystal form after annealing at 110EC 45 min |
|---|---|---|---|---|
| Heating of Lamotrigine Solvates/Hydrates | | | | |
| E methanolate | 18 | E | 27 | A |
| J isopropanolate | 19 | Amorphous | 28 | A |
| H ethanolate | 20 | H | 29 | A |
| L acetonate | 21 | A | 30 | A |
| K THF solvate | 22 | K | 31 | A |
| N hydrate | 23 | A | 32 | A |
| M DMA solvate | 24 | M | 33 | M |
| C DMF monosolvate | 25 | P (20% LOD) | 34 | A + P |
| O ⅔ methanolate | 26 | — | 35 | A |

The invention will be better understood from the following experimental details. These examples are provided to illustrate specific embodiments of the present invention but they are not intended to be limiting in any way.

EXAMPLES

Novel Crystal Forms Obtained by Heating Lamotrigine Solvates

Example 1

Form A-Anhydrous

Lamotrigine form L acetonate (about 200 mg) was heated at about 110° C. for the period of about 1 hour, to produce lamotrigine form A.

Example 2

Form A-Anhydrous

Lamotrigine form N hydrate (about 200 mg) was heated at about 110° C. for the period of about 1 hour, to produce lamotrigine form A.

Example 3

Form P-Monosolvate of DMF

Lamotrigine form C monosolvate of (about 200 mg) was heated at about 80° C. for a period of about 1 hour, to produce lamotrigine form P monosolvate of DMF.

Example 4

Amorphous

Lamotrigine form J isopropanolate of (about 200 mg) was heated at about 80° C. for a period of about 1 hour, to produce lamotrigine amorphous.

Novel Solvated Forms Obtained by Crystallization Using Solvent/Anti-Solvent Technique

Example 5

Form B-Monosolvate of DMF

Lamotrigine anhydrous (about 10 grams) was dissolved in about 8 gram DMF at about 70° C., about 24 grams of water were then added at about 0° C. to precipitate the solid. The suspension was stirred about 10 minutes, and the solid was filtrated under reduced pressure to produce lamotrigine form B.

Example 6

Form C-Sesquisolvate of DMF

Lamotrigine anhydrous about 0.5 gram was dissolved in about 8 gram DMF at about 70° C., about 25 grams of chloroform were then added at about 0° C. to precipitate the solid. The suspension was stirred about 10 minutes, and the solid was filtrated under reduced pressure to produce lamotrigine form C.

Example 7

Form C-Sesquisolvate of DMF

Lamotrigine anhydrous about 0.5 gram was dissolved in about 8 gram DMF at about 70° C., about 20 grams of toluene were then added at about 0° C. to precipitate the solid. The suspension was stirred about 10 minutes, and the solid was filtrated under reduced pressure to produce lamotrigine form C.

Example 8

Form C-Sesquisolvate of DMF

Lamotrigine anhydrous about 0.13 gram was dissolved in about 8 grams DMF at about 70° C., about 20 grams of toluene were then added at about 0° C. to precipitate the solid. The suspension was stirred about 10 minutes, and the solid was filtrated under reduced pressure to produce lamotrigine form C.

Example 9

Form C-Sesquisolvate of DMF

Lamotrigine anhydrous about 0.5 gram was dissolved in about 8 grams DMF at about 70° C., about 20 grams of acetone were then added at about 0° C. to precipitate the solid. The suspension was stirred about 10 minutes, and the solid was filtrated under reduced pressure to produce lamotrigine form C.

Example 10

Form C-Sesquisolvate of DMF

Lamotrigine anhydrous about 0.8 gram was dissolved in about 8 gram DMF at about 70° C., about 20 grams of acetone were then added at about 0° C. to precipitate the solid. The suspension was stirred about 10 minutes, and the solid was filtrated under reduced pressure to produce lamotrigine form C.

Example 11

Form D-$\frac{2}{3}$ Solvate of DMF

Lamotrigine anhydrous about 0.54 gram was dissolved in about 8 gram DMF at about 70° C., about 24 grams of water were then added at about 0° C. to precipitate the solid. The suspension was stiffed about 10 minutes, and the solid was filtrated under reduced pressure to produce lamotrigine form D.

Example 12

Form E-$\frac{2}{3}$ Methanolate

Lamotrigine anhydrous about 0.13 gram was dissolved in about 8 grams MeOH at about 55° C., about 20 grams of toluene were then added at about 0° C. to precipitate the solid. The suspension was stirred about 10 minutes, and the solid was filtrated under reduced pressure to produce lamotrigine form E.

Example 13

Form E1-$\frac{2}{3}$ Ethanolate

Lamotrigine anhydrous about 0.13 mg was dissolved in EtOH at about 55° C., of toluene were added at about 0° C. to precipitate the solid. The suspension was stirred about 10 minutes, and the solid was filtrated under reduced pressure to produce lamotrigine form E1.

Example 14

Form F-$\frac{1}{3}$ Solvate of Acetone

Lamotrigine anhydrous about 0.12 mg was dissolved in about 8 grams acetone at about 70° C., about 20 grams of cyclohexane were added at about 0° C. to precipitate the solid. The suspension was stirred about 10 minutes, and the solid was filtrated under reduced pressure to produce lamotrigine form F.

Novel Solvated/Hydrates Forms Obtained by Slurry of Lamotrigine

Example 15

Form C-Monosolvate of DMF

In a 0.1 L three-necked bottomed round flask equipped with a mechanical stirrer, a condenser and a thermometer charge about 2 grams of lamotrigine anhydrous and about 10 ml of DMF. The suspension is stirred about 24 hours without heating at about 25 EC then the solid phase is separated by filtration, producing form C.

Example 16

Form H-Monosolvate of Ethanol

In a 0.1 L three-necked bottomed round flask equipped with a mechanical stirrer, a condenser and a thermometer charge about 2 grams of lamotrigine anhydrous and about 80 mL of ethanol. The suspension is stirred about 24 hours without heating at about 25 EC then the solid phase is separated by filtration, producing form H.

Example 17

Form K-Solvate of THF

In a 0.1 L three-necked bottomed round flask equipped with a mechanical stirrer, a condenser and a thermometer charge about 2 grams of lamotrigine anhydrous and about 37 mL of THF. The suspension is stirred about 24 hours without heating at about 25 EC then the solid phase is separated by filtration, producing form K.

Example 18

Form L-Solvate of Acetone

In a 0.1 L three-necked bottomed round flask equipped with a mechanical stirrer, a condenser and a thermometer charge about 1 gram of lamotrigine anhydrous and about 700 mL of acetone were charged. The suspension was stirred about 24 hours without heating at about 25 EC. After this time a solution appeared. This solution was concentrated to dryness, about 50 mL of acetone were added, then the solid phase was separated by filtration, producing form L.

Example 19

Form M-Solvate of DMA

In a 0.1 L three-necked bottomed round flask equipped with a mechanical stirrer, a condenser and a thermometer charge about 2 grams of lamotrigine anhydrous and about 12.5 ml of DMA. The suspension is stirred about 24 hours without heating at about 25 EC then the solid phase is separated by filtration, producing form M.

Example 20

Form N-Hydrate

In a 0.1 L three-necked bottomed round flask equipped with a mechanical stirrer, a condenser and a thermometer charge about 2 grams of lamotrigine anhydrous and about 833 mL of water. The suspension is stirred about 24 hours without heating at about 25 EC then the solid phase is separated by filtration, producing form N.

Novel Crystal Form Obtained by Crystallization of Solution

Example 21

Form O-⅔ Methanolate

In a 1 L three-necked bottomed round flask equipped with a mechanical stirrer, a condenser and a thermometer about 20 grams of lamotrigine crude and about 680 ml of methanol were charged. The suspension was heated to reflux (about 65 EC) when a clear solution was obtained. The solution was cooled slowly during about 5.5 hours to about 25 EC and filtered. After filtration and drying at about 60 EC for about 17 hours at about 10 mmHg lamotrigine form 0 was obtained.

Example 22

Crystallization from Isopropanol of Form J Isopropanolate

In a 1 L three-necked bottomed round flask equipped with a mechanical stirrer, a condenser and a thermometer, about 20 grams of lamotrigine anhydrous and about 70 ml of isopropanol were charged. The suspension was heated to reflux (about 65 EC) when a clear solution was obtained. The solution was cooled slowly during about 5.5 hours to about 25 EC and filtered. After filtration and drying at about 50 EC for about 17 hours at about 10 mmHg lamotrigine form J was obtained.

Example 23

In a 1 L three-necked bottomed round flask equipped with a mechanical stirrer, a condenser and a thermometer about 20 grams of lamotrigine anhydrous and about 58 ml of ethanol were charged. The suspension was heated to reflux (about 65 EC) when a clear solution was obtained. The solution was cooled slowly during about 5.5 hours to about 25 EC and filtered. After filtration and drying at about 50 EC for about 17 hours at about 10 mmHg lamotrigine form H was obtained.

Example 24

Form Q-Monosolvate of Isopropanol

Lamotrigine anhydrous about 62 grams were dissolved in about 100 grams isopropanol to form a solution. The solution was refluxed for about 5 minutes and cooled to room temperature (5° C. per minute). The solid was separated by filtration to produce lamotrigine form Q.

Example 25

Form R-Monosolvate of Methyl-Isobutyl-Ketone (MIBK)

Lamotrigine anhydrous about 0.4 gram was suspended in about 45 grams methyl-isobutyl-ketone (MIBK) to form a mixture. The mixture was refluxed for about 5 minutes and then cooled under magnetic stirring (5° C. per minute). The solid was left in the mother liquor 24 hours and then filtered under reduced pressure to produce lamotrigine form R.

Example 26

Form S-Anhydrous

Lamotrigine anhydrous about 0.2 gram was suspended in about 150 grams DMC to form a mixture. The mixture was suspended for about 60 minutes and cooled to room temperature (5° C. per minute) under magnetic stirring. The solid was left in the mother liquor for about 24 hours and the solid was separated by filtration to produce lamotrigine form S.

Example 27

Form U-Monosolvate of MTBE

Lamotrigine anhydrous about 0.0546 gram were suspended in about 80 grams MTBE to form a solution. The solution was refluxed for about 5 minutes and cooled (20° C. per minute) under stirring. The solid was separated by filtration at room temperature to produce lamotrigine form U.

Pharmaceutical Composition of Lamotrigine

In addition to the active ingredient(s), lamotrigine pharmaceutical compositions of the present invention may contain one or more excipients. Excipients are added to the composition for a variety of purposes.

Diluents increase the bulk of a solid pharmaceutical composition and may make a pharmaceutical dosage form containing the composition easier for the patient and care giver to handle. Diluents for solid compositions include, for example, microcrystalline cellulose (e.g. Avicel[7]), microfine cellulose, lactose, starch, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit[7]), potassium chloride, powdered cellulose, sodium chloride, sorbitol and talc.

Solid pharmaceutical compositions that are compacted into a dosage form like a tablet may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel[7]), hydroxypropyl methyl cellulose (e.g. Methocel[7]), liquid glucose, magnesium aluminum silicate, maltodextrin, methylcellulose, polymethacrylates, povidone (e.g. Kollidon[7], Plasdone[7]), pregelatinized starch, sodium alginate and starch.

The dissolution rate of a compacted solid pharmaceutical composition in the patient=s stomach may be increased by the addition of a disintegrant to the composition. Disintegrants include alginic acid, carboxymethylcellulose calcium, carboxymethylcellulose sodium (e.g. Ac-Di-Sol[7], Primellose[7]), colloidal silicon dioxide, croscarmellose sodium, crospovidone (e.g. Kollidon[7], Polyplasdone[7]), guar gum, magnesium aluminum silicate, methyl cellulose, microcrystalline cellulose, polacrilin potassium, powdered cellulose, pregelatinized starch, sodium alginate, sodium starch glycolate (e.g. Explotab[7]) and starch.

Glidants can be added to improve the flow properties of non-compacted solid compositions and improve the accuracy of dosing. Excipients that may function as glidants include colloidal silicon dixoide, magnesium trisilicate, powdered cellulose, starch, talc and tribasic calcium phosphate.

When a dosage form such as a tablet is made by compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid ethyl maltol, and tartaric acid.

Compositions may also be colored using any pharmaceutically acceptable colorant to improve their appearance and/or facilitate patient identification of the product and unit dosage level.

Selection of excipients and the amounts to use may be readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable route in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches and losenges as well as liquid syrups, suspensions and elixirs. An especially preferred dosage form of the present invention is a tablet.

The invention has been described with reference to its preferred embodiments. All cited references are incorporated herein by reference in their entirety. From this description, those skilled in the art may appreciate changes that could be made in the invention that does not depart from the scope and spirit of the invention.

What is claimed is:

1. Crystalline form E of 6-(2,3-dichlorophenyl)-1,2,4-triazine-3,5-diamine, characterized by an X-ray powder diffraction pattern having peaks at about 9.5, 11.5, 13.8, 23.2 and 26.7 ±0.2 degrees two-theta.

2. The crystalline form E of 6-(2,3-dichlorophenyl)-1,2,4-triazine-3,5-diamine according to claim 1, further characterized by an X-ray powder diffraction pattern having other typical peaks at about 13.0, 14.3, 14.9, 15.7, 17.9, 19.4, 20.9, 24.5, 25.6, 27.3 and 32.2±0.2 degrees two-theta.

Figure 4:
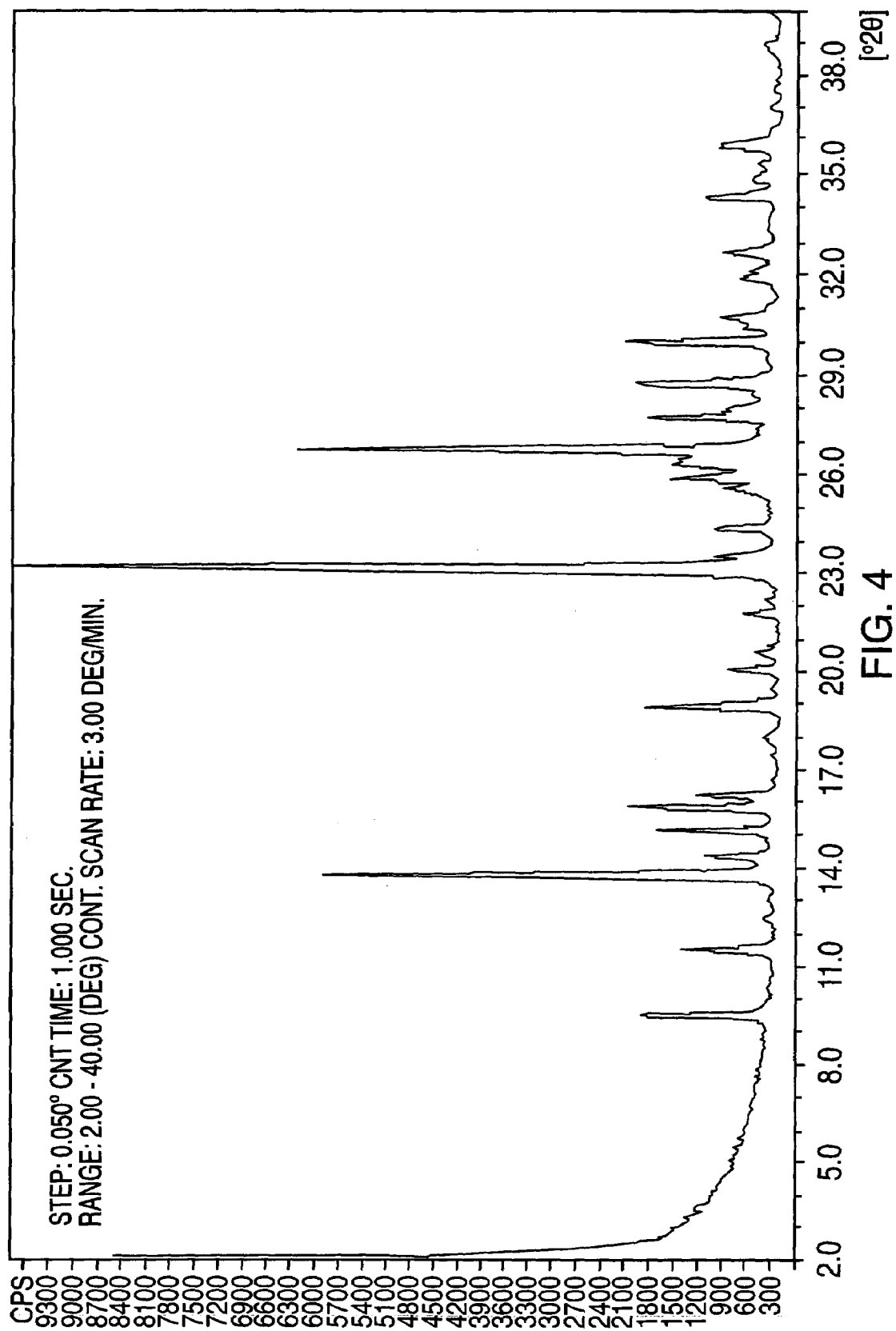
FIG. 4 shows the X-ray diffraction pattern of lamotrigine form E.
Figure 5:
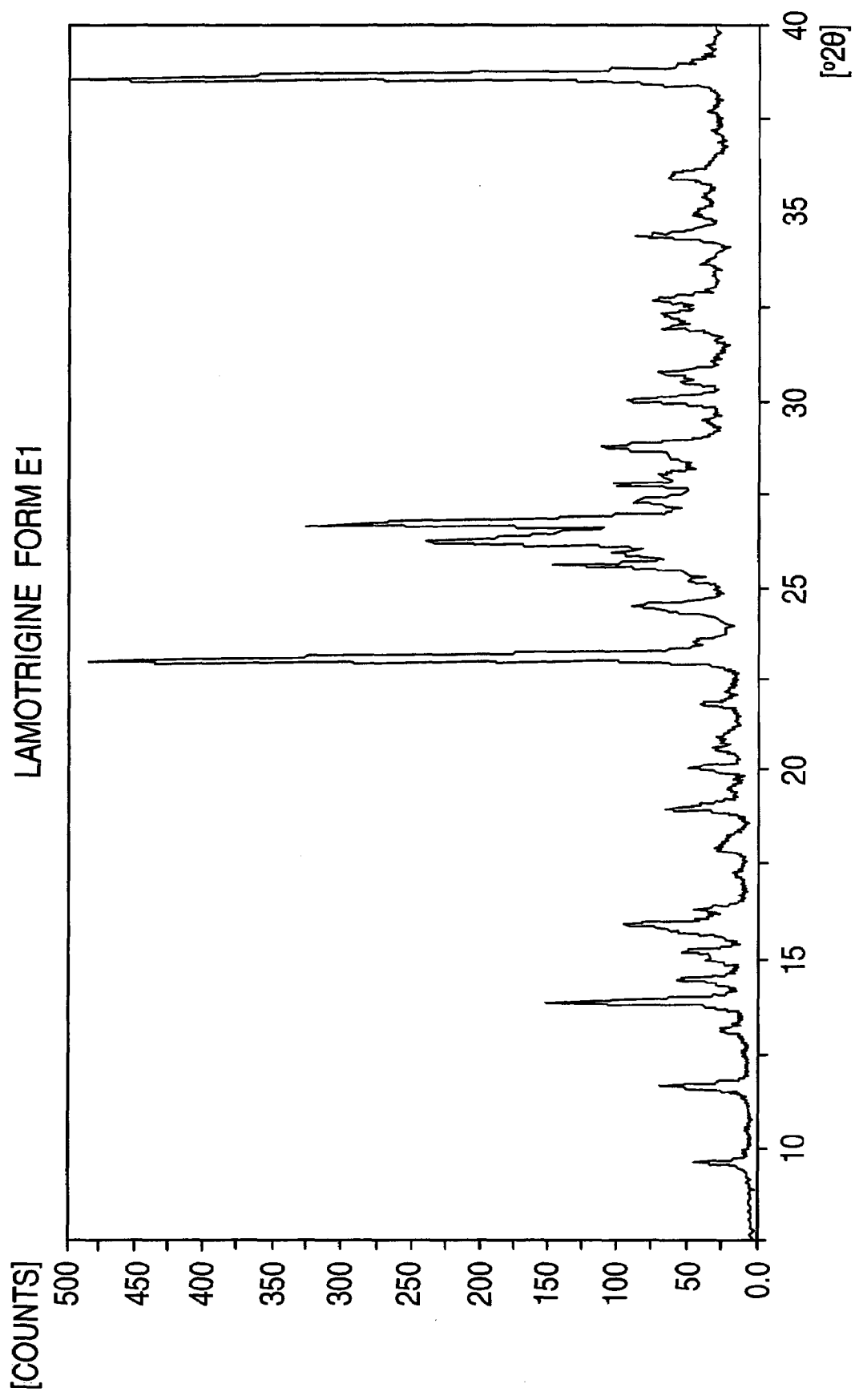
FIG. 5 shows the X-ray diffraction pattern of lamotrigine form E1.
Figure 6:
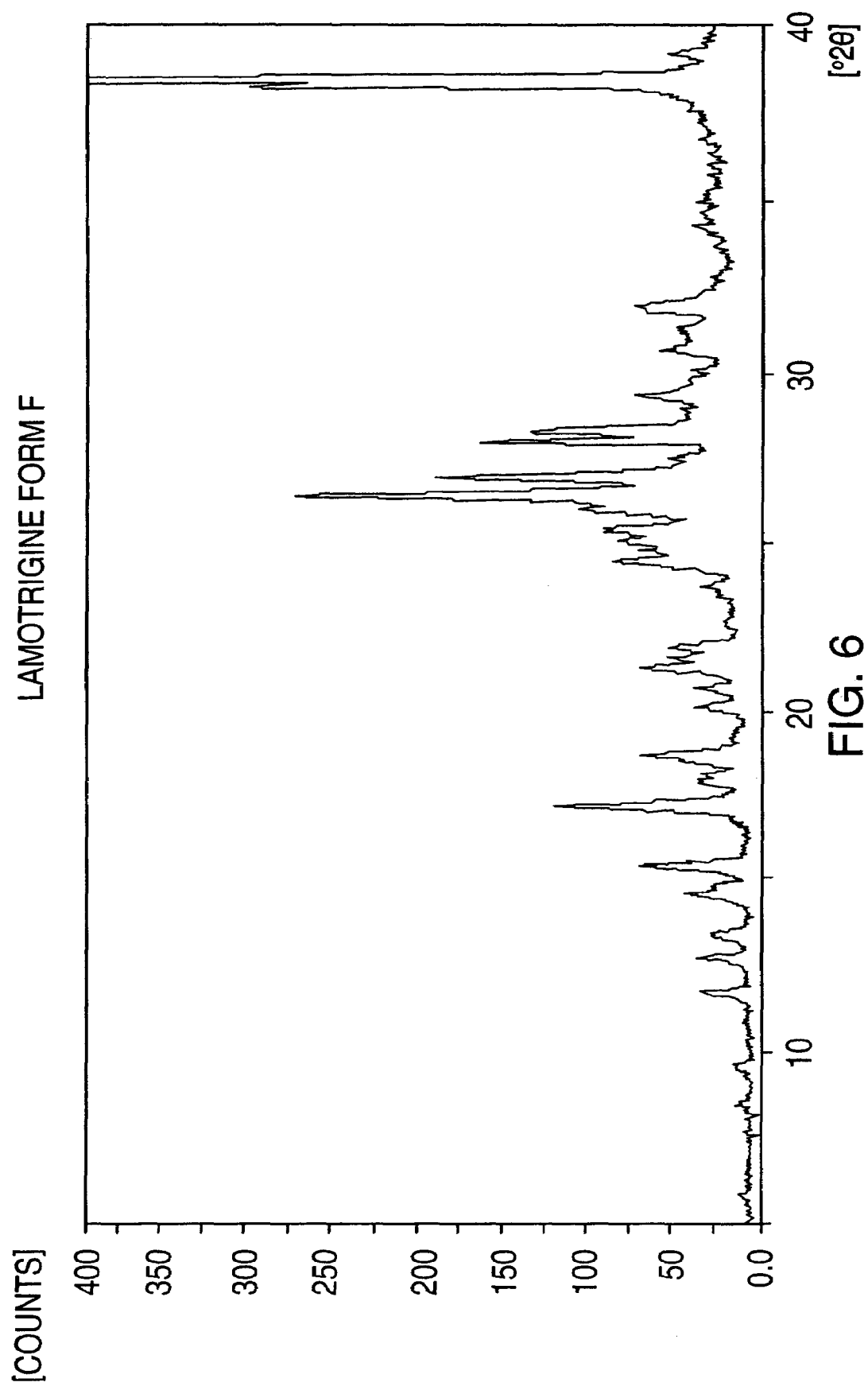
FIG. 6 shows the X-ray diffraction pattern of lamotrigine form F.
Figure 7:
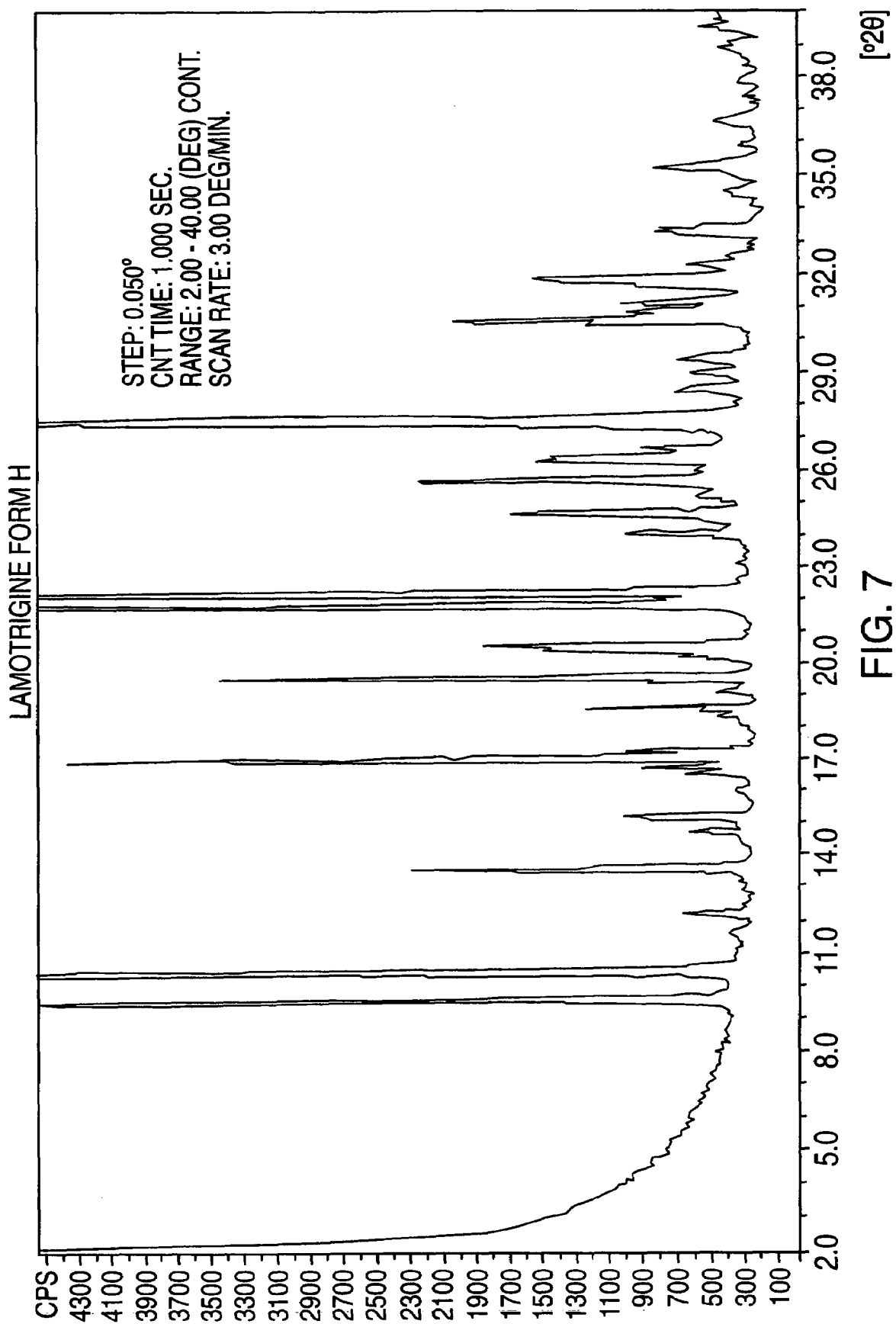
FIG. 7 shows the X-ray diffraction pattern of lamotrigine form H.
Figure 8:
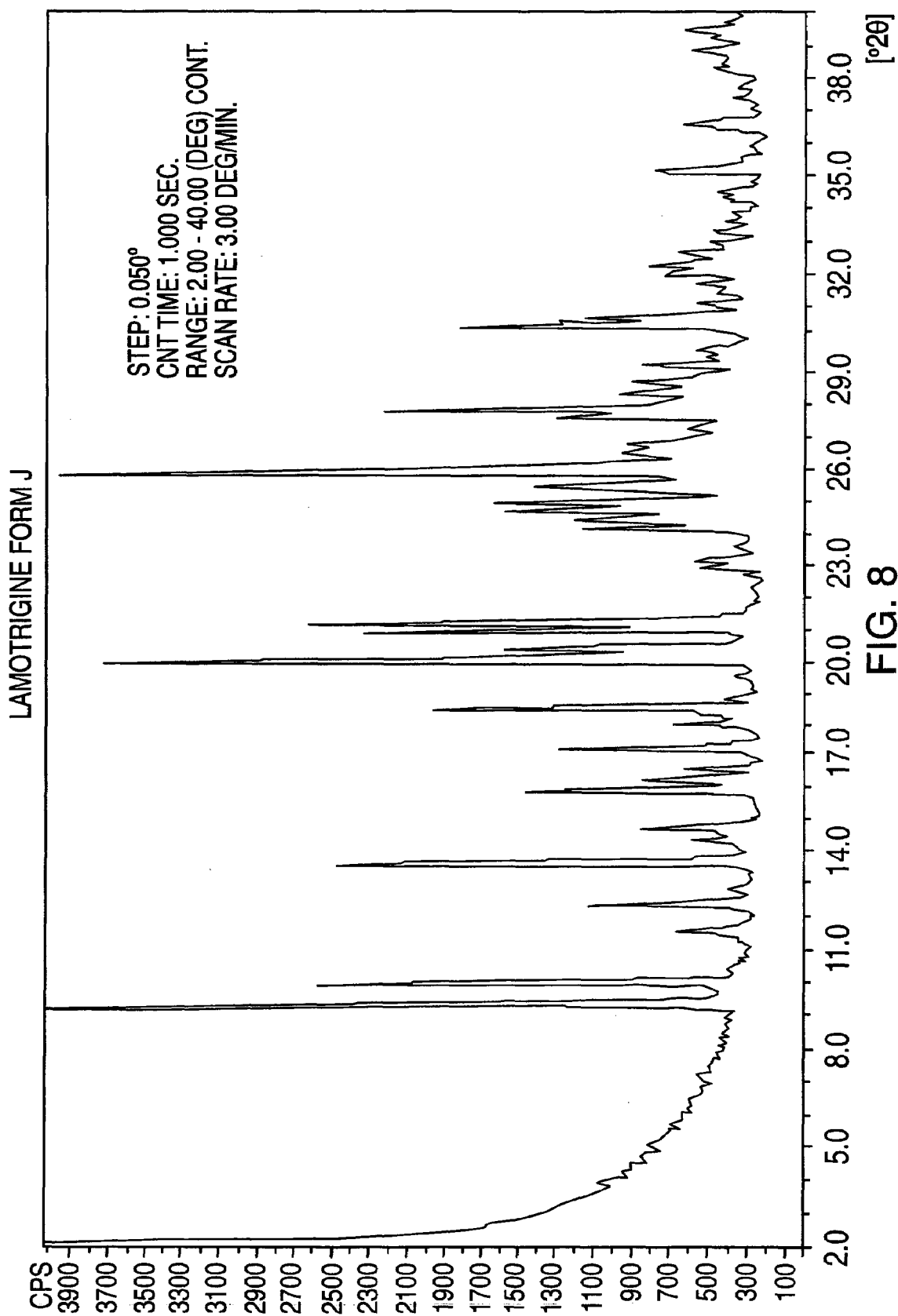
FIG. 8 shows the X-ray diffraction pattern of lamotrigine form J.
Figure 9:
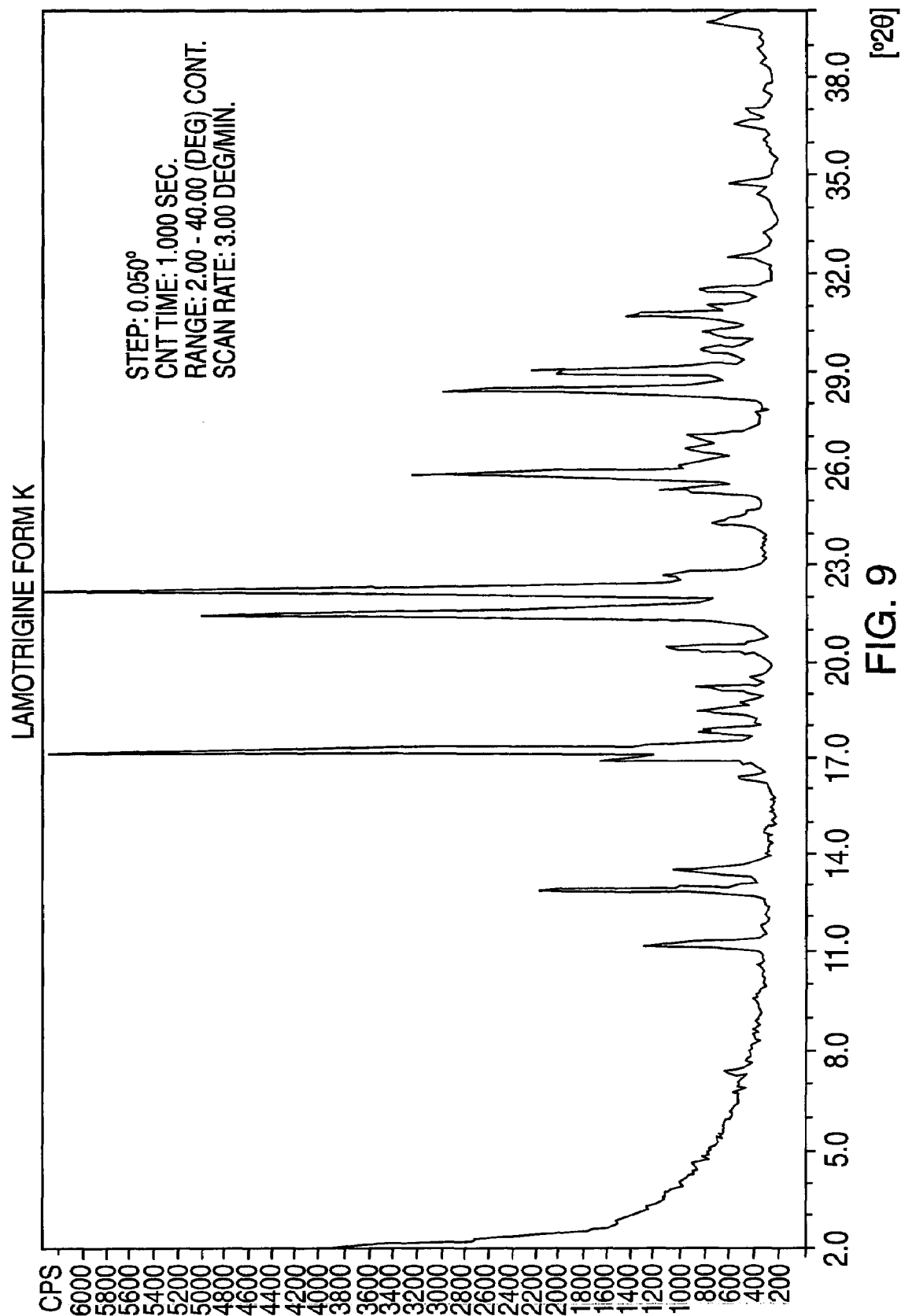
FIG. 9 shows the X-ray diffraction pattern of lamotrigine form K.
Figure 10:
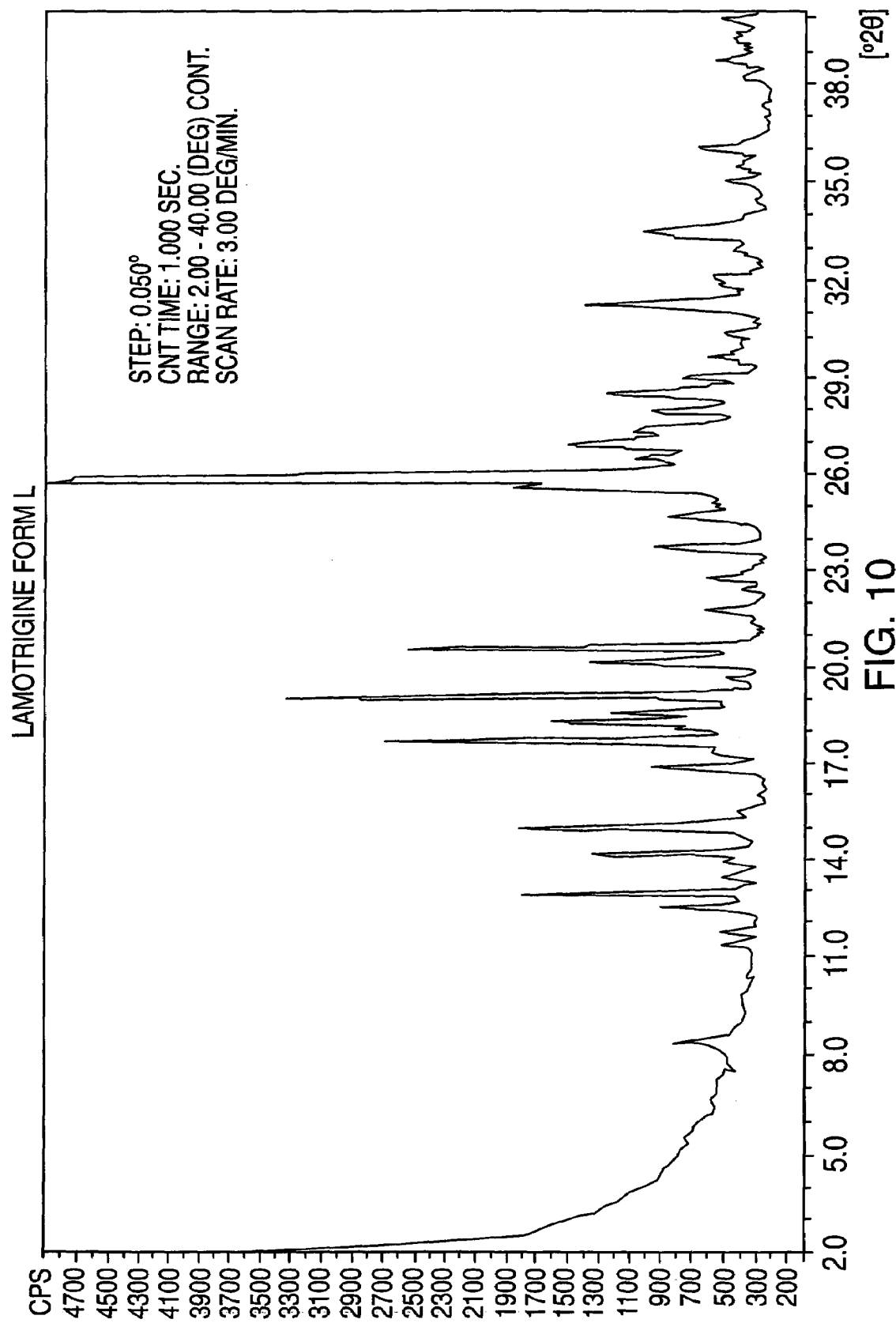
FIG. 10 shows the X-ray diffraction pattern of lamotrigine form L.
Figure 11:
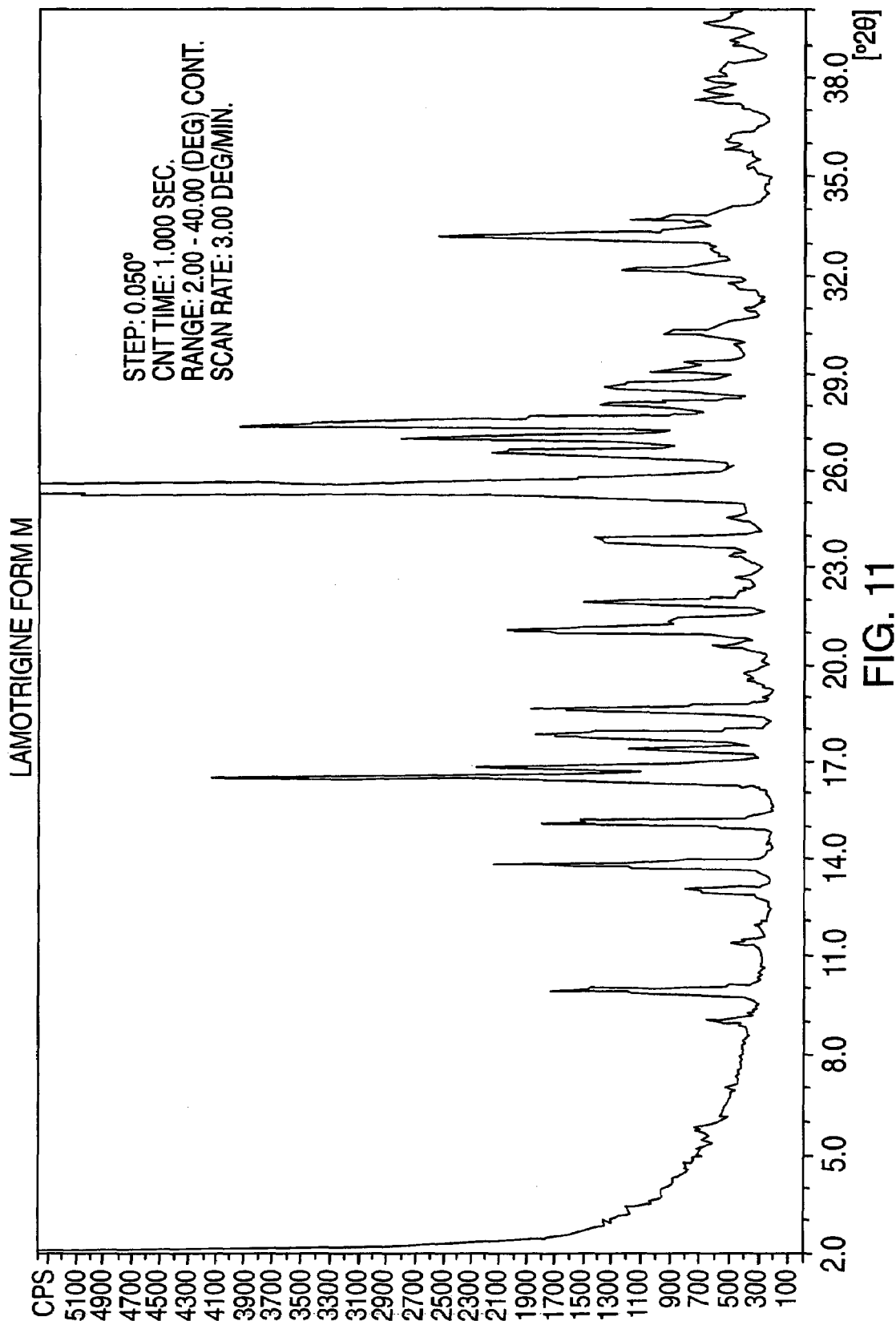
FIG. 11 shows the X-ray diffraction pattern of lamotrigine form M.
Figure 12:
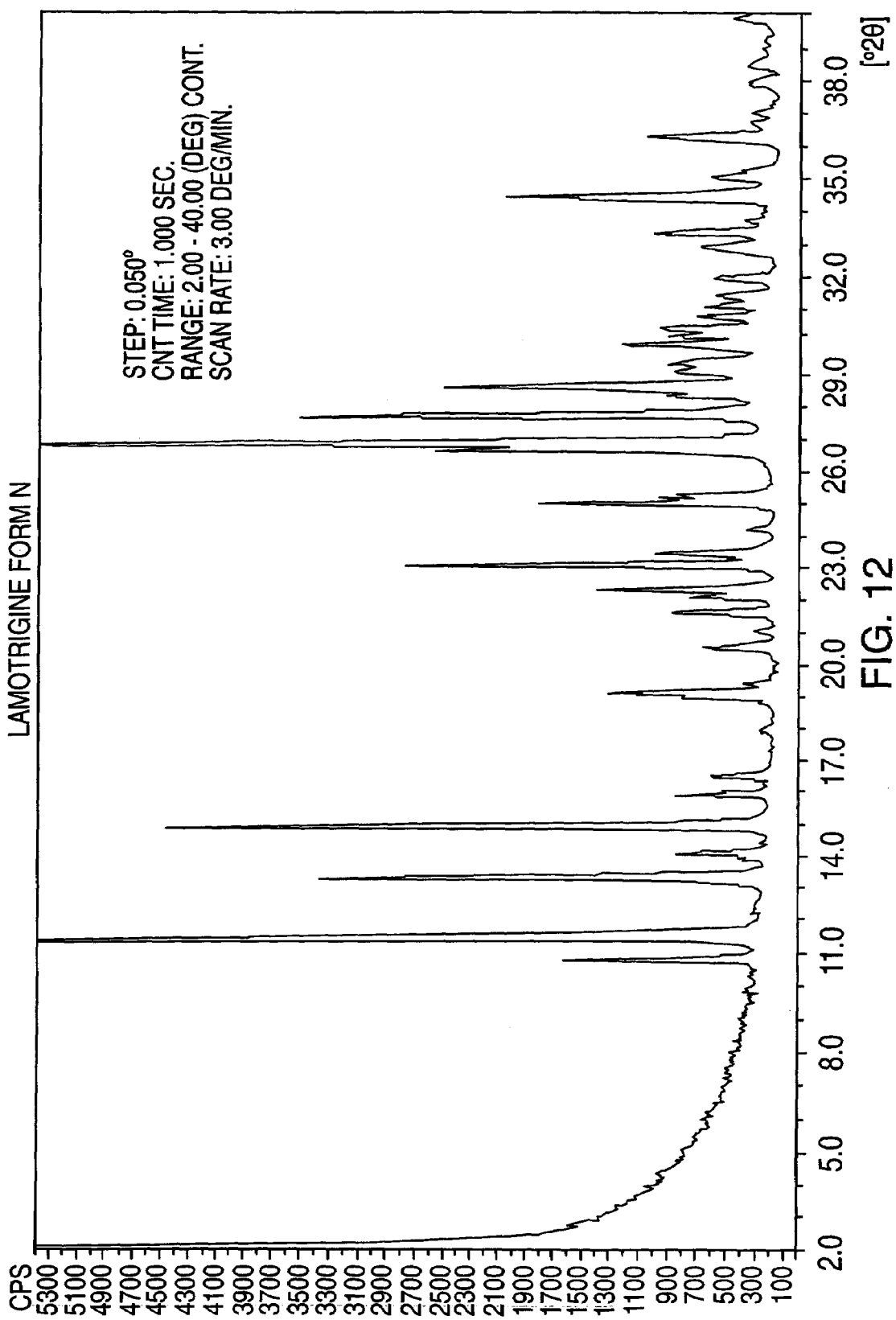
FIG. 12 shows the X-ray diffraction pattern of lamotrigine form N.

3. Crystalline form E of 6-(2,3-dichlorophenyl)-1,2,4-triazine-3,5-diamine, characterized by an X-ray powder diffraction pattern as in FIG. 4.

4. The crystalline form E of 6-(2,3-dichlorophenyl)-1,2,4-triazine-3,5-diamine according to claim 1, wherein the crystalline form E of 6-(2,3-dichlorophenyl)-1,2,4-triazine-3,5-diamine is a ⅔ methanolate.

5. Crystalline form O of 6-(2,3-dichlorophenyl)-1,2,4-triazine-3,5-diamine, characterized by an X-ray powder diffraction pattern having peaks at about 9.5, 13.7, 23.0, 26.7, and 28.7 ±0.2 degrees two-theta.

6. The crystalline form O of 6-(2,3-dichlorophenyl)-1,2,4-triazine-3,5-diamine according to claim 5, further characterized by an X-ray powder diffraction pattern having other typical peaks at about 8.5, 11.4, 14.2, 15.7, 18.0, 18.9, 24.2, 25.6, 25.9, 27.7, 30.0, 30.7, 32.6, 34.3, and 34.8±0.2 degrees two-theta.

Figure 13:
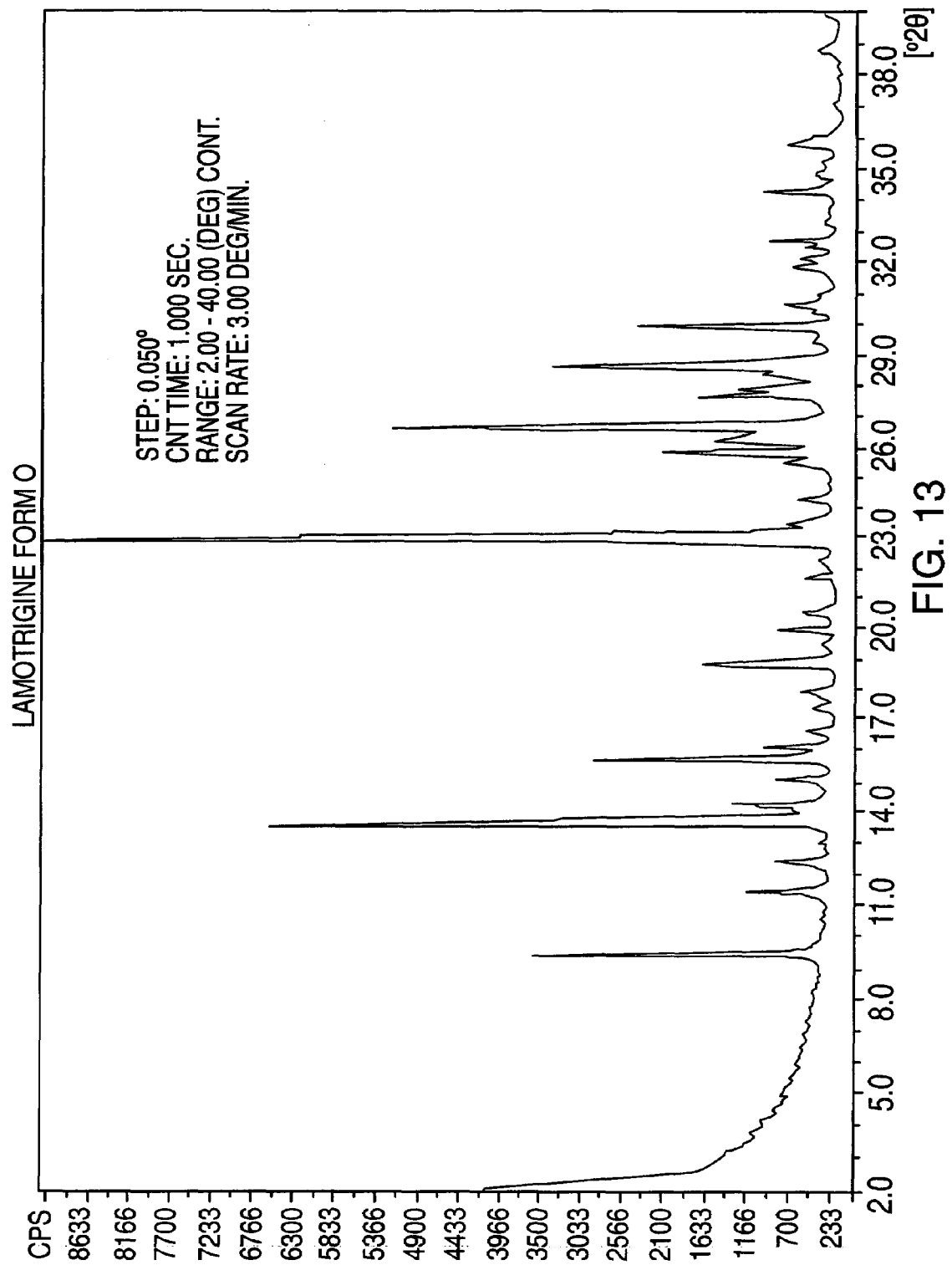
FIG. 13 shows the X-ray diffraction pattern of lamotrigine form O.
Figure 14:
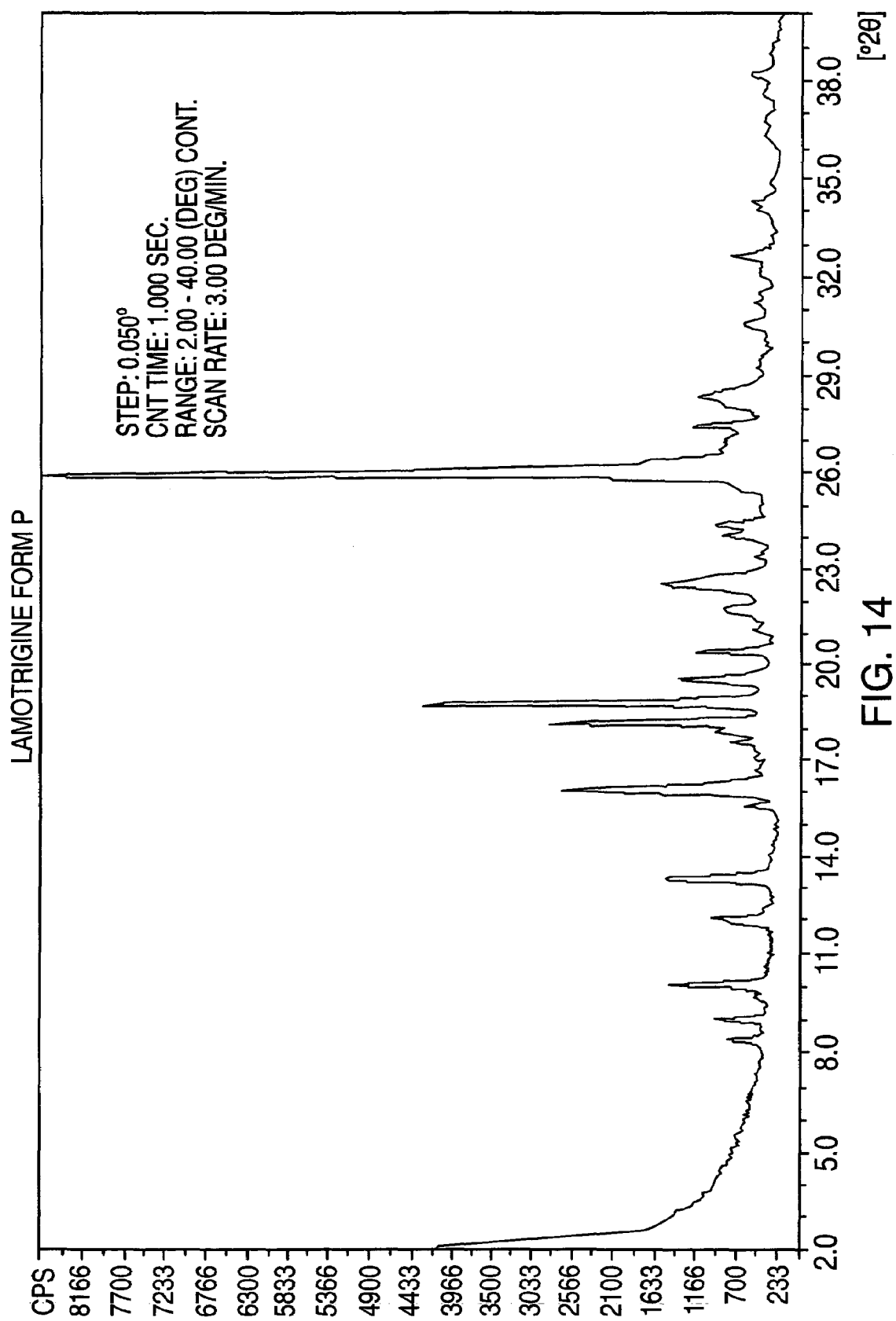
FIG. 14 shows the X-ray diffraction pattern of lamotrigine form P.
Figure 15:
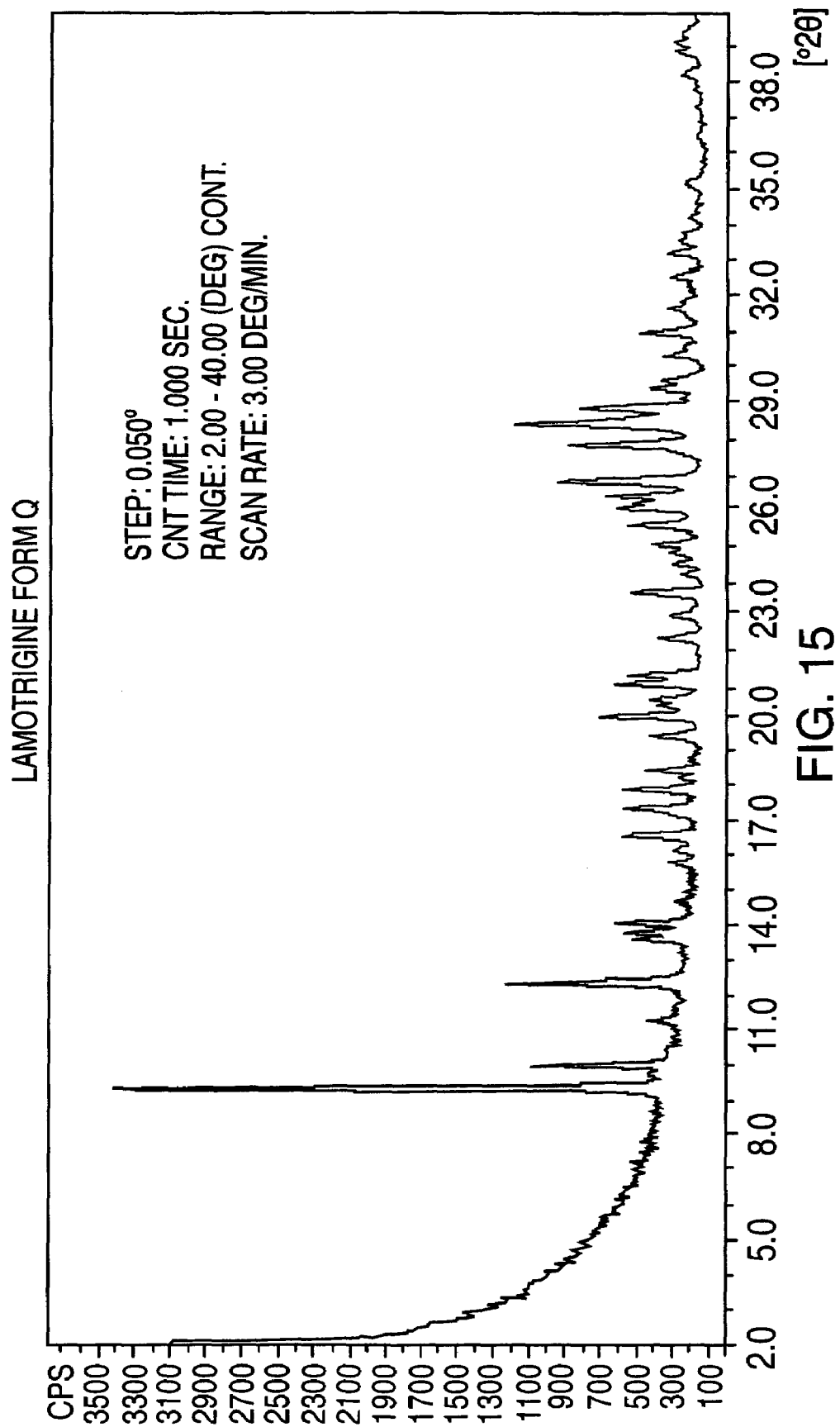
FIG. 15 shows the X-ray diffraction pattern of lamotrigine form Q.
Figure 16:
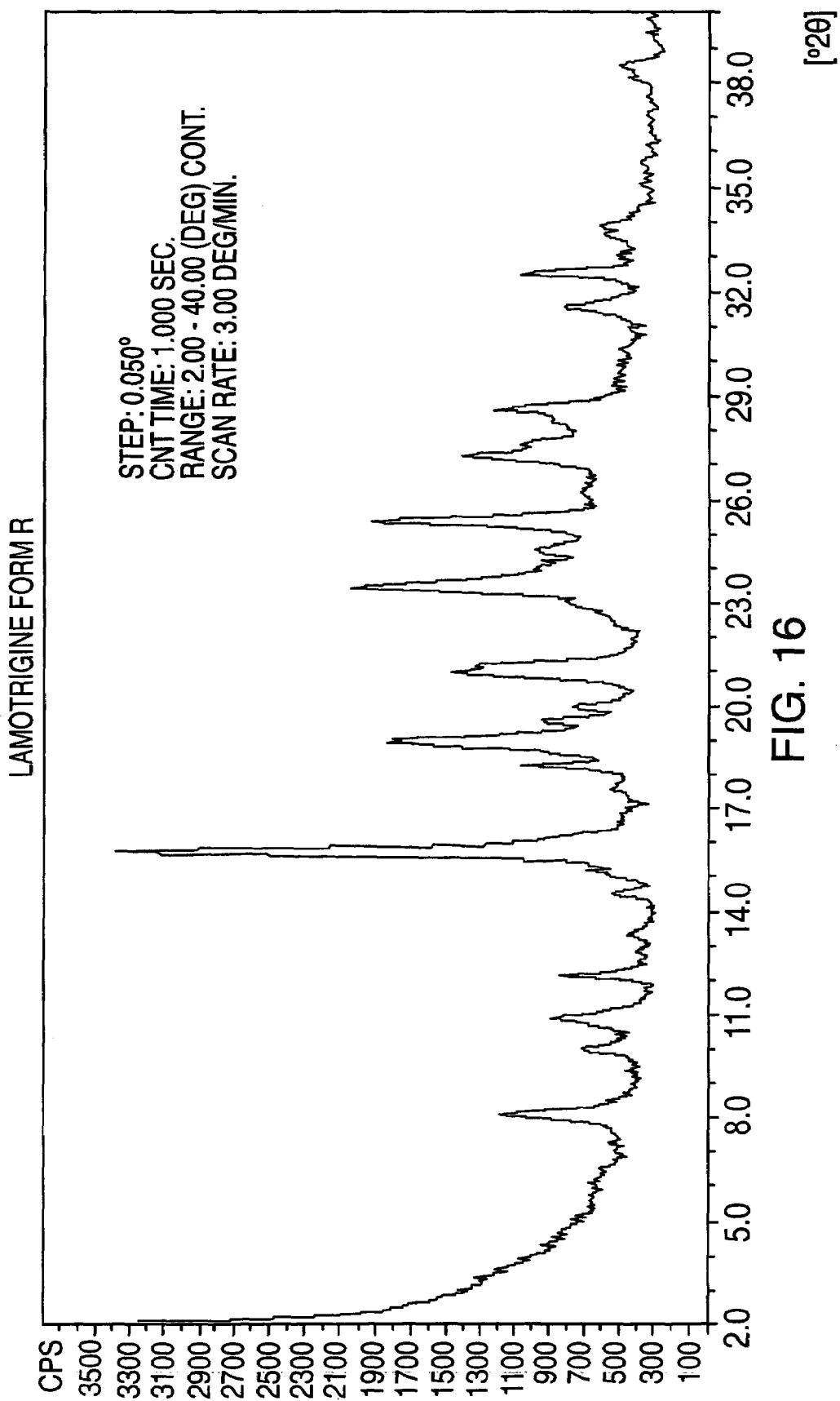
FIG. 16 shows the X-ray diffraction pattern of lamotrigine form R.
Figure 17:
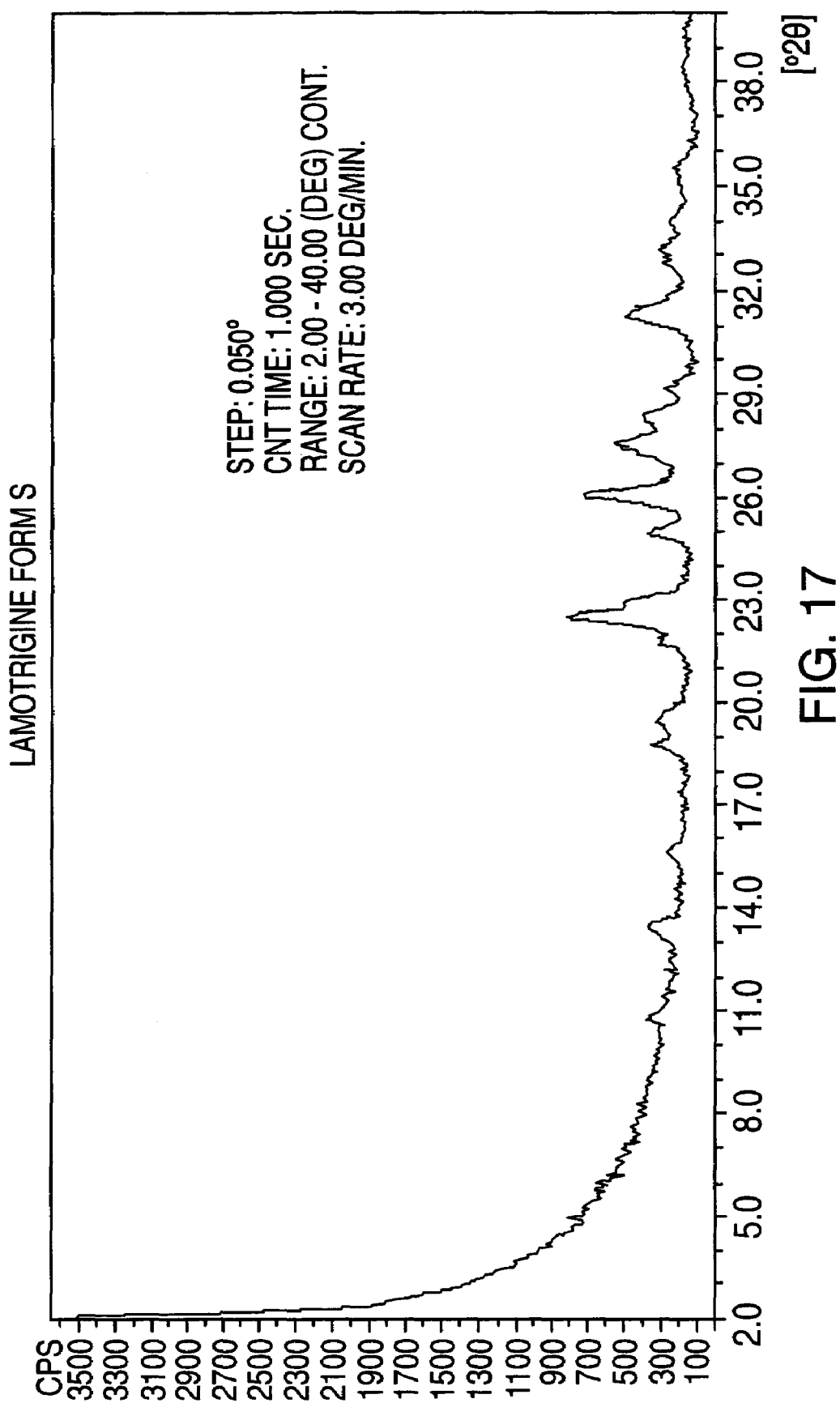
FIG. 17 shows the X-ray diffraction pattern of lamotrigine form S.
Figure 18:
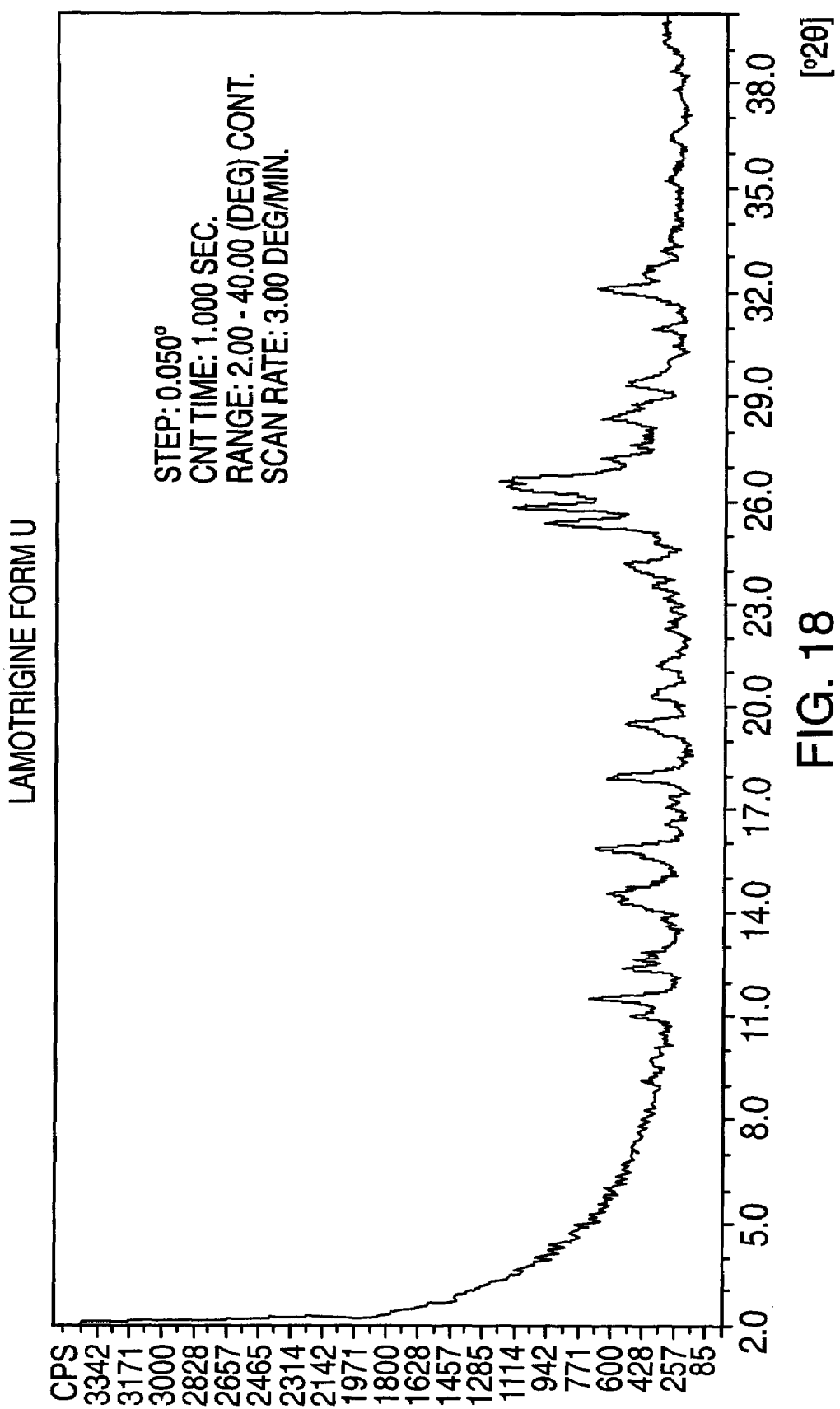
FIG. 18 shows the X-ray diffraction pattern of lamotrigine form U.

7. Crystalline form O of 6-(2,3-dichlorophenyl)-1,2,4-triazine-3,5-diamine, characterized by an X-ray powder diffraction pattern as in FIG. 13.

8. The crystalline form O of 6-(2,3-dichlorophenyl)-1,2,4-triazine-3,5-diamine according to claim 5, wherein the crystalline form O of 6-(2,3-dichlorophenyl)-1,2,4-triazine-3,5-diamine is a ⅔ methanolate.

9. A solid pharmaceutical composition comprising a therapeutically effective amount of a solvated crystalline form of 6-(2,3-dichlorophenyl)-1,2,4-triazine-3,5-diamine selected from the group consisting of crystalline form E of 6-(2,3-dichlorophenyl)-1,2,4-triazine-3,5-diamine characterized by an X-ray powder diffraction pattern having peaks at about 9.5, 11.5, 13.8, 23.2 and 26.7 ±0.2 degrees two-theta and crystalline form O of 6-(2,3-dichlorophenyl)-1,2,4-triazine-3,5-diamine characterized by an X-ray powder diffraction pattern having peaks at about 9.5, 13.7, 23.0, 26.7, and 28.7 ±0.2 degrees two-theta.

10. A method for treating a patient suffering from epilepsia by administering a therapeutically effective amount of a crystalline form of 6-(2,3-dichlorophenyl)-1,2,4-triazine-3,5-diamine selected from the group consisting of lamotrigine crystalline form E of 6-(2,3-dichlorophenyl)-1,2,4-triazine-3,5-diamine characterized by an X-ray powder diffraction pattern having peaks at about 9.5, 11.5, 13.8, 23.2 and 26.7±0.2 degrees two-theta and crystalline form O of 6-(2,3-dichlorophenyl)-1,2,4-triazine-3,5-diamine characterized by an X-ray powder diffraction pattern having peaks at about 9.5, 13.7, 23.0, 26.7, and 28.7±0.2 degrees two-theta.

11. A method for preparing crystalline form E of 6-(2,3-dichlorophenyl)-1,2,4-triazine-3,5-diamine characterized by an X-ray powder diffraction pattern having peaks at about 9.5, 11.5, 13.8, 23.2 and 26.7±0.2 degrees two-theta, comprising the steps of
1) dissolving anhydrous 6-(2,3-dichlorophenyl)-1,2,4-triazine-3,5-diamine in methanol at about 55° C.; and
2) precipitating the crystalline form E of 6-(2,3-dichlorophenyl)-1,2,4-triazine-3,5-diamine by adding toluene at about 0° C. to obtain the crystalline form E of 6-(2,3-dichlorophenyl)-1,2,4-triazine-3,5-diamine.

12. A method of preparing crystalline form O of 6-(2,3-dichlorophenyl)-1,2,4-triazine-3,5-diamine characterized by an X-ray powder diffraction pattern having peaks at about 9.5, 13.7, 23.0, 26.7, and 28.7±0.2 degrees two-theta, comprising the steps of
1) dissolving anhydrous 6-(2,3-dichlorophenyl)-1,2,4-triazine-3,5-diamine in methanol to form a solution;
2) heating the solution to about 65° C.;
3) cooling the solution to about 25° C. for about 5.5 hours;
4) filtering the solution; and
5) drying the solution at about 60° C. for about 17 hours at about 10 mmHg to obtain the crystalline form O of 6-(2,3-dichlorophenyl)-1,2,4-triazine-3,5-diamine.

13. A method for prepaxing anhydrous crystalline 6-(2,3-dichlorophenyl)-1,2,4-triazine-3,5-diamine, comprising heating at least one crystalline solvate of 6-(2,3-dichlorophenyl)-1,2,4-triazine-3,5-diamine selected from the group consisting of crystalline form E of 6-(2,3-dichlorophenyl)-1,2,4-triazine-3,5-diamine characterized by an X-ray powder diffraction pattern having peaks at about 9.5, 11.5, 13.8, 23.2 and 26.7±0.2 degrees two-theta and crystalline form O of 6-(2,3-dichlorophenyl)-1,2,4-triazine-3,5-diamine characterized by an X-ray powder diffraction pattern having peaks at about 9.5, 13.7, 23.0, 26.7, and 28.7±0.2 degrees two-theta at an elevated temperature sufficient to remove methanol from the crystalline solvate to produce the anhydrous crystalline 6-(2,3-dichlorophenyl)-1,2,4-triazine-3,5-diamine.

* * * * *

UNITED STATES PATENT AND TRADEMARK OFFICE
CERTIFICATE OF CORRECTION

PATENT NO.        : 7,390,807 B2
APPLICATION NO.   : 11/045355
DATED             : June 24, 2008
INVENTOR(S)       : Garti et al.

It is certified that error appears in the above-identified patent and that said Letters Patent is hereby corrected as shown below:

Column 19, line 16, change "6-(2.3-diclorophenyl)-1,2,4-triazine-3,5-diamine," to --6-(2,3-diclorophenyl)-1,2,4-triazine-3,5-diamine--

Column 20, line 25, change "prepaxing," to --preparing--

Signed and Sealed this

Twenty-second Day of December, 2009

David J. Kappos
*Director of the United States Patent and Trademark Office*